United States Patent
Nam et al.

(10) Patent No.: US 10,682,111 B2
(45) Date of Patent: Jun. 16, 2020

(54) MEDICAL IMAGE DISPLAY DEVICE AND MEDICAL IMAGE PROCESSING METHOD

(71) Applicant: Samsung Electronics Co., Ltd., Suwon-si, Gyeonggi-do (KR)

(72) Inventors: Woo-hyun Nam, Seoul (KR); Ji-hun Oh, Hwaseong-si (KR); Yong-sup Park, Seoul (KR); Jae-sung Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 68 days.

(21) Appl. No.: 15/753,051

(22) PCT Filed: Jun. 9, 2016

(86) PCT No.: PCT/KR2016/006087
§ 371 (c)(1),
(2) Date: Feb. 15, 2018

(87) PCT Pub. No.: WO2017/030276
PCT Pub. Date: Feb. 23, 2017

(65) Prior Publication Data
US 2018/0235563 A1    Aug. 23, 2018

(30) Foreign Application Priority Data

Aug. 17, 2015 (KR) .......................... 10-2015-0115661
Apr. 12, 2016 (KR) .......................... 10-2016-0044817

(51) Int. Cl.
*G06K 9/00* (2006.01)
*A61B 6/00* (2006.01)
(Continued)

(52) U.S. Cl.
CPC .............. *A61B 6/5229* (2013.01); *A61B 5/00* (2013.01); *A61B 5/055* (2013.01); *A61B 5/742* (2013.01);
(Continued)

(58) Field of Classification Search
None
See application file for complete search history.

(56) References Cited

U.S. PATENT DOCUMENTS 8,983,179 B1   3/2015 Yu et al.
2007/0244393 A1   10/2007 Oshiki et al.
(Continued)

FOREIGN PATENT DOCUMENTS

KR   10-2014-0105101 A   9/2014
KR   10-2014-0120236 A   10/2014
WO      2014/155299 A1   10/2014

OTHER PUBLICATIONS

European Search Report dated Jul. 2, 2018, issued in European Application No. 16837218.3.
(Continued)

*Primary Examiner* — Wei Wen Yang
(74) *Attorney, Agent, or Firm* — Jefferson IP Law, LLP

(57) ABSTRACT

Disclosed are a medical image display device for displaying a screen including a medical image and a medical image processing method thereof, the medical image display device comprising: a display configured to display a first medical image obtained by photographing an object comprising at least one anatomical entity; and at least one processor configured to extract reference region information corresponding to the anatomical entity from at least one second medical image used as a reference image for the first medical image, detect a region corresponding to the anatomical entity from the first medical image based on the
(Continued)

extracted reference region information, and control the display to display the region of the detected anatomical entity to be distinguishable from at least one region unrelated to the anatomical entity.

15 Claims, 27 Drawing Sheets

(51) Int. Cl.
| | |
|---|---|
| A61B 5/055 | (2006.01) |
| A61B 5/00 | (2006.01) |
| G06T 7/00 | (2017.01) |
| G06T 7/33 | (2017.01) |
| G06T 7/30 | (2017.01) |
| A61B 8/08 | (2006.01) |
| A61B 6/03 | (2006.01) |

(52) U.S. Cl.
CPC .......... *A61B 6/461* (2013.01); *A61B 8/5238* (2013.01); *G06T 7/0014* (2013.01); *G06T 7/30* (2017.01); *G06T 7/337* (2017.01); *A61B 6/032* (2013.01); *A61B 6/481* (2013.01); *G06T 7/0012* (2013.01); *G06T 2207/10081* (2013.01); *G06T 2207/10088* (2013.01); *G06T 2207/10132* (2013.01); *G06T 2207/30004* (2013.01)

(56) References Cited

U.S. PATENT DOCUMENTS

| | | | |
|---|---|---|---|
| 2008/0025638 A1* | 1/2008 | Chen | G06T 7/35 |
| | | | 382/284 |
| 2013/0116538 A1* | 5/2013 | Herzog | A61B 8/4254 |
| | | | 600/407 |
| 2014/0029812 A1 | 1/2014 | Kriston et al. | |
| 2014/0200433 A1 | 7/2014 | Choi et al. | |
| 2015/0317452 A1* | 11/2015 | Kozuka | G06F 19/321 |
| | | | 705/2 |

OTHER PUBLICATIONS

European Office Action dated May 8, 2019, issued in European Patent Application No. 16837218.3.
European Office Action dated Apr. 7, 2020, issued in European Patent Application No. 16837218.3.

\* cited by examiner

FIG. 16
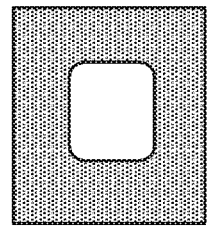
REGISTERED IMAGE
or
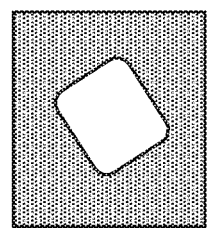
REGISTERED IMAGE
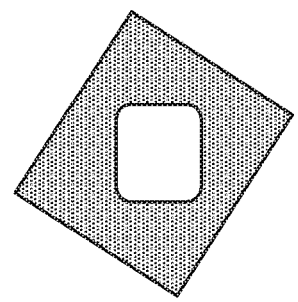
MOVING IMAGE
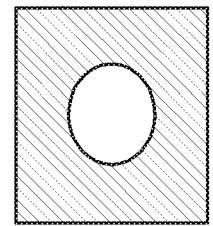
FIXED IMAGE

FIXED IMAGE    MOVING IMAGE    REGISTERED IMAGE

MEDICAL IMAGE DISPLAY DEVICE AND MEDICAL IMAGE PROCESSING METHOD

TECHNICAL FIELD

The present disclosure relates to a medical image display device for displaying a screen including a medical image and a medical image processing method thereof.

BACKGROUND ART

A medical image display device refers to a device for obtaining an internal structure of an object as an image. The medical image display device is a noninvasive examination device, which obtains and processes images of structural details, internal organs, fluid flow, etc. inside a human body and shows them to a user. A doctor or the like user can diagnose a patient's health condition and disease through a medical image output from the medical image display device.

As the medical image display device, there are a magnetic resonance imaging (MRI) device for providing a magnetic resonance image, a computed tomography (CT) device, an X-ray device, an ultrasound device, etc.

The MRI device refers to a device for using a magnetic field to take an image of an subject, which has been widely used for making an accurate disease diagnosis since it can stereoscopically show disks, joints, nerves, ligaments, etc. as well as bones at a desired angle.

The MRI device employs a high-frequency multi-coil with radio frequency (RF) coils, a permanent magnet, a gradient coil, etc. to obtain a magnetic resonance (MR) signal. Further, a magnetic resonance image is restored by sampling the MR signal.

The CT device has been also widely used for a precise diagnosis of diseases since it has advantages of providing a cross-section image of an object and showing the internal structure (e.g. organs such as a kidney, a lung, etc.) of the object without overlapping as compared with general X-ray devices.

The CT device emits an X-ray to an object and senses the X-ray passed through the object. Further, the sensed X-ray is used to restore an image.

The X-ray device shows an internal image of an object by a method of emitting an X-ray to an object and detecting the X-ray penetrating the object.

The ultrasound device transmits an ultrasound signal to an object and receives the ultrasound signal from the object, thereby forming a two- or three-dimensional ultrasound image of an interesting entity inside the object.

DISCLOSURE

Technical Problem

As described above, medical images obtained by various medical image display devices represent an object in various ways according to the kinds and image-taking methods of medical image display device. A doctor reads the medical images and diagnoses a patient's diseases or health conditions. Therefore, there is a need of providing a medical image display device for facilitating a doctor's diagnosis so that a doctor can selectively read a medical image suitable to diagnose a patient.

Technical Solution

According to one embodiment of the present disclosure, a medical image display device comprises a display configured to display a first medical image obtained by photographing an object comprising at least one anatomical entity; and at least one processor configured to extract reference region information corresponding to the anatomical entity from at least one second medical image used as a reference image for the first medical image, detect a region corresponding to the anatomical entity from the first medical image based on the extracted reference region information, and control the display to display the region of the detected anatomical entity to be distinguishable from at least one region unrelated to the anatomical entity. Thus, there is a provided a function of distinguishably displaying an entity, which has not been identified in the medical image, based on information extracted from the reference image.

The processor may generate a third medical image comprising display region information about the detected anatomical entity in the first medical image by registration between the first medical image and the second medical image, and control the display to display the region of the detected anatomical entity to be distinguishable from at least one region unrelated to the anatomical entity in the third medical image generated based on the display region information. Thus, it is possible to distinguishably display an entity through an image generated based on medical registration.

The anatomical entity may be given in plural, and the display may display regions of the plurality of anatomical entities to be distinguishable. Thus, it is convenient to make a diagnosis since unidentifiable entities are distinguishable.

The plurality of anatomical entities may include at least one of the blood vessel and the lymph node. Thus, the blood vessel and the lymph node, which are important factors for clinic determination, are distinguishably displayed.

The first medical image may be a non-contrast medical image. Thus, it is possible to distinguishably display the anatomical entities in the non-contrast medical image obtained by photographing the object who is concerned with side effects the contrast medium.

The second medical image may be a contrast-enhanced medical image. Thus, the contrast-enhanced medical image, which is easy to distinguish between entities through region division, can be utilized as the reference image.

The second medical image may be a medical image obtained by photographing the same object as that of the first medical image at another point of time. Thus, a patient's past history can be applicable to the current diagnosis.

The display may display the region of the detected anatomical entity to be distinguishable with at least one of a color, a pattern, a pointer, a highlight and an animation effect from at least one region unrelated to the anatomical entity. Thus, there are provided various distinguishable display functions according to a user's tastes.

The distinguishable display for the region of the anatomical entity may be activated or inactivated by a user's selection. Thus, convenience in a user's selection is promoted with regard to the entity distinguishable display function.

There is further provided a user input for receiving a user's input, and the processor may control the display to adjust a display level for distinguishing between the anatomical entities in response to a user's input. Thus, there is provided a function corresponding to a user's taste.

The processor may further detect a lesion expansion region from the region of the anatomical entity, and control the display to display the detected lesion expansion region to be distinguishable within the region of the anatomical entity.

Thus, information about severity lesion is further provided, thereby facilitating a lesion diagnosis.

The processor may employ a brightness level of pixels in the second medical image to extract the reference region information corresponding to the anatomical entity. Thus, the previously stored information about the image is efficiently utilized to thereby acquire necessary information.

The processor may employ a predetermined transformation model parameter for performing image registration to maximize a result value of a similarity measurement function between the first medical image and the second medical image. Thus, the registered image generated as a result of the image registration process is improved in accuracy.

The processor may employ a predetermined transformation model parameter for performing image registration to minimize a result value of a cost function between the first medical image and the second medical image. Thus, the registered image generated as a result of the image registration process is decreased in probability of an error.

The processor may make coordinate systems of the first medical image and the second medical image be subjected to mapping, and perform homogeneous registration, in which image characteristics of the second medical image are maintained and matched with the first medical image, with regard to the first medical image and the second medical image of which the coordinate systems are subjected to the mapping. Thus, there is provided a registration image in which the lymph node and the blood vessel are distinguishably displayed.

The processor may further perform in-homogeneous registration, in which image characteristics of the second medical image are transformed and exactly matched with the first medical image, with regard to the first medical image and the second medical image which are subjected to the homogeneous registration. Thus, even quantification and results about the expansion of the lesion within the lymph node are provided to a user.

According to one embodiment of the present disclosure, a medical image processing method comprises displaying a first medical image obtained by photographing an object comprising at least one anatomical entity; extracting reference region information corresponding to the anatomical entity from at least one second medical image used as a reference image for the first medical image; and detecting a region corresponding to the anatomical entity from the first medical image based on the extracted reference region information, and displaying the region of the detected anatomical entity to be distinguishable from at least one region unrelated to the anatomical entity. Thus, there is a provided a function of distinguishably displaying an entity, which has not been identified in the medical image, based on information extracted from the reference image.

The medical image processing method may further comprise generating a third medical image comprising display region information about the detected anatomical entity in the first medical image by registration between the first medical image and the second medical image, wherein the distinguishable displaying comprises displaying the region of the detected anatomical entity to be distinguishable from at least one region unrelated to the anatomical entity in the third medical image generated based on the display region information. Thus, it is possible to distinguishably display an entity through an image generated based on medical registration.

The anatomical entity may be given in plural, and the display may display regions of the plurality of anatomical entities to be distinguishable. Thus, it is convenient to make a diagnosis since unidentifiable entities are distinguishable.

The plurality of anatomical entities may include at least one of the blood vessel and the lymph node. Thus, the blood vessel and the lymph node, which are important factors for clinic determination, are distinguishably displayed.

The first medical image may be a non-contrast medical image. Thus, it is possible to distinguishably display the anatomical entities in the non-contrast medical image obtained by photographing the object who is concerned with side effects the contrast medium.

The second medical image may be a contrast-enhanced medical image. Thus, the contrast-enhanced medical image, which is easy to distinguish between entities through region division, can be utilized as the reference image.

The second medical image may be a medical image obtained by photographing the same object as that of the first medical image at another point of time. Thus, a patient's past history can be applicable to the current diagnosis.

The distinguishable displaying may display the region of the detected anatomical entity to be distinguishable with at least one of a color, a pattern, a pointer, a highlight and an animation effect from at least one region unrelated to the anatomical entity. Thus, there are provided various distinguishable display functions according to a user's tastes.

The distinguishable display for the region of the anatomical entity may be activated or inactivated by a user's selection. Thus, convenience in a user's selection is promoted with regard to the entity distinguishable display function.

There is further provided receiving a user's input for adjusting a display level for distinguishing between the anatomical entities. Thus, there is provided a function corresponding to a user's taste.

There are further provided detecting a lesion expansion region from the regions of the distinguishably displayed anatomical entities, and controlling the display to display the detected lesion expansion region to be distinguishable within the region of the anatomical entity. Thus, information about severity lesion is further provided, thereby facilitating a lesion diagnosis.

The extraction of the reference region information may comprise employing a brightness level of pixels in the second medical image to extract the reference region information corresponding to the anatomical entity. Thus, the previously stored information about the image is efficiently utilized to thereby acquire necessary information.

The generation of the third medical image may include employing a predetermined transformation model parameter for performing image registration to maximize a result value of a similarity measurement function between the first medical image and the second medical image. Thus, the registered image generated as a result of the image registration process is improved in accuracy.

The generation of the third medical image may include employing a predetermined transformation model parameter for performing image registration to minimize a result value of a cost function between the first medical image and the second medical image. Thus, the registered image generated as a result of the image registration process is decreased in probability of an error.

The generation of the third medical image may include making coordinate systems of the first medical image and the second medical image be subjected to mapping, and performing homogeneous registration, in which image characteristics of the second medical image are maintained and matched with the first medical image, with regard to the first medical image and the second medical image of which the coordinate systems are subjected to the mapping. Thus, there is provided a registration image in which the lymph node and the blood vessel are distinguishably displayed.

The generation of the third medical image may include performing in-homogeneous registration, in which image characteristics of the second medical image are transformed and exactly matched with the first medical image, with regard to the first medical image and the second medical image which are subjected to the homogeneous registration. Thus, even quantification and results about the expansion of the lesion within the lymph node are provided to a user.

According to one embodiment of the present disclosure, a recording medium in which a program for performing a medical image processing method is recorded as a computer-readable program, the medical image processing method comprises displaying a first medical image obtained by photographing an object comprising at least one anatomical entity; extracting reference region information corresponding to the anatomical entity from at least one second medical image used as a reference image for the first medical image; and detecting a region corresponding to the anatomical entity from the first medical image based on the extracted reference region information, and displaying the region of the detected anatomical entity to be distinguishable from at least one region unrelated to the anatomical entity. Thus, there is a provided a function of distinguishably displaying an entity, which has not been identified in the medical image, based on information extracted from the reference image.

The medical image processing method may further comprise generating a third medical image comprising display region information about the detected anatomical entity in the first medical image by registration between the first medical image and the second medical image, wherein the distinguishable displaying comprises displaying the region of the detected anatomical entity to be distinguishable from at least one region unrelated to the anatomical entity in the third medical image generated based on the display region information. Thus, it is possible to distinguishably display an entity through an image generated based on medical registration.

The anatomical entity may be given in plural, and the display may display regions of the plurality of anatomical entities to be distinguishable. Thus, it is convenient to make a diagnosis since unidentifiable entities are distinguishable.

The plurality of anatomical entities may include at least one of the blood vessel and the lymph node. Thus, the blood vessel and the lymph node, which are important factors for clinic determination, are distinguishably displayed.

The first medical image may be a non-contrast medical image. Thus, it is possible to distinguishably display the anatomical entities in the non-contrast medical image obtained by photographing the object who is concerned with side effects the contrast medium.

The second medical image may be a contrast-enhanced medical image. Thus, the contrast-enhanced medical image, which is easy to distinguish between entities through region division, can be utilized as the reference image.

The second medical image may be a medical image obtained by photographing the same object as that of the first medical image at another point of time. Thus, a patient's past history can be applicable to the current diagnosis.

The distinguishable displaying may display the region of the detected anatomical entity to be distinguishable with at least one of a color, a pattern, a pointer, a highlight and an animation effect from at least one region unrelated to the anatomical entity. Thus, there are provided various distinguishable display functions according to a user's tastes.

The distinguishable display for the region of the anatomical entity may be activated or inactivated by a user's selection. Thus, convenience in a user's selection is promoted with regard to the entity distinguishable display function.

There is further provided receiving a user's input for adjusting a display level for distinguishing between the anatomical entities. Thus, there is provided a function corresponding to a user's taste.

There are further provided detecting a lesion expansion region from the regions of the distinguishably displayed anatomical entities, and controlling the display to display the detected lesion expansion region to be distinguishable within the region of the anatomical entity. Thus, information about severity lesion is further provided, thereby facilitating a lesion diagnosis.

The extraction of the reference region information may comprise employing a brightness level of pixels in the second medical image to extract the reference region information corresponding to the anatomical entity. Thus, the previously stored information about the image is efficiently utilized to thereby acquire necessary information.

The generation of the third medical image may include employing a predetermined transformation model parameter for performing image registration to maximize a result value of a similarity measurement function between the first medical image and the second medical image. Thus, the registered image generated as a result of the image registration process is improved in accuracy.

The generation of the third medical image may include employing a predetermined transformation model parameter for performing image registration to minimize a result value of a cost function between the first medical image and the second medical image. Thus, the registered image generated as a result of the image registration process is decreased in probability of an error.

The generation of the third medical image may include making coordinate systems of the first medical image and the second medical image be subjected to mapping, and performing homogeneous registration, in which image characteristics of the second medical image are maintained and matched with the first medical image, with regard to the first medical image and the second medical image of which the coordinate systems are subjected to the mapping. Thus, there is provided a registration image in which the lymph node and the blood vessel are distinguishably displayed.

The generation of the third medical image may include performing in-homogeneous registration, in which image characteristics of the second medical image are transformed and exactly matched with the first medical image, with regard to the first medical image and the second medical image which are subjected to the homogeneous registration. Thus, even quantification and results about the expansion of the lesion within the lymph node are provided to a user.

Advantageous Effects

According to one embodiment of the present disclosure, it is possible to apply the follow-up examination for the lymph node to patients whose kidneys function poorly and who are difficult to actively get the contrast medium.

Further, probability of a misdiagnosis of lymph node-related diseases is low even though it is based on the non-contrast image, thereby improving a diagnosis system (under/over-estimation) and enhancing accuracy of a diagnosis.

Further, the present embodiments are applicable to a non-contrast image for general examination, and utilized in a diagnosis or the like of cancer metastasis and the like cancer diseases.

DESCRIPTION OF DRAWINGS

FIG. 16 is a view for conceptually illustrating a homogeneous registration process.

BEST MODE

Figure 1:
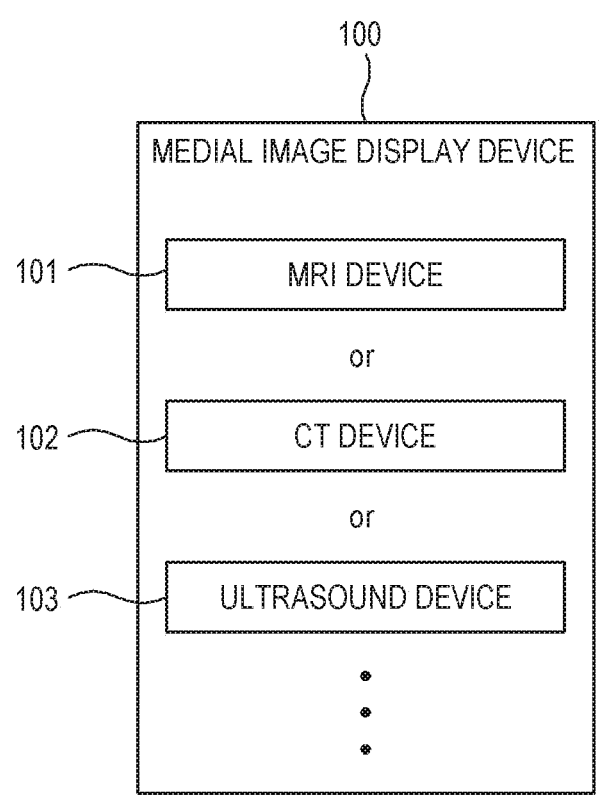
FIG. 1 is a view for describing a medical image display device according to one embodiment of the present disclosure.

Below, exemplary embodiments will be described with reference to accompanying drawings to such an extent as to be easily realized by a person having an ordinary knowledge in the art. The present inventive concept is not limited to the embodiments set forth herein, and may be materialized variously.

Terms to be used in the following descriptions will be selected as general terms currently used as widely as possible taking functions of elements into account, but may be varied depending on intent of those skilled in the art, precedents, the advent of new technology, etc. In particular, there may be a term voluntarily selected by the applicant. In this case, the meaning of the term will be explained in detail through the relevant detailed descriptions. Therefore, the terms set forth herein have to be read in light of its meaning and content throughout the following descriptions rather than naming.

In the following descriptions, terms such as "include" or "have" refer to presence of features, numbers, steps, operations, elements or combination thereof, and do not exclude presence or addition of one or more other features, numbers, steps, operations, elements or combination thereof.

A "portion" set forth herein refers to software or hardware such as FPGA or ASIC, and performs certain roles. However, the meaning of the "portion" is not limited to software or hardware. The "portion" may be configured to be present in a storage medium for addressing or may be configured to reproduce one or more processors. For example, the "portion" includes software elements, object-oriented software elements, class elements, task elements and the like elements, and processes, functions, attributes, procedures, subroutines, segments of a program code, drivers, firmware, a microcode, a circuit, data, a database, data structures, tables, arrays and variables. The function provided in the elements and the "portions" may be carried out by combining fewer elements and "portions" or may be subdivided by additional elements and "portions".

For clarity, elements not directly related to the elements of the exemplary embodiment may be omitted, and like numerals refer to like elements throughout.

In this specification, an "image" may indicate multi-dimensional data configured with discrete image elements (for example, pixels in a two-dimensional (2D) image and voxels in a three-dimensional (3D) image). For example, the image may include a medical image and the like of an object, obtained by X-ray, CT, MRI, ultrasound and other medical imaging systems.

Further, in this specification, an "object" may include a human or an animal, or a part of the human or animal. For example, the object may include a liver, a heart, a uterus, a brain, a breast, an abdomen and the like organs, or a blood vessel. Further, the "object" may include a phantom. The phantom refers to a material having a volume, which is very approximate to the density and the effective atomic number of living things, and may include a sphere phantom having similar properties to a human body.

Further, in this specification, a "user" refers to a medical expert such as a doctor, a nurse, a medical laboratory technologist, a medical image specialist, etc. or a technician of repairing a medical device, but is not limited thereto.

For clarity of the present disclosure in association with the drawings, portions not directly related to the elements of the present disclosure may be omitted, and like numerals refer to like elements throughout.

FIG. 1 is a view for describing a medical image display device 100 according to one embodiment of the present disclosure.

According to one embodiment of the present disclosure, the medical image display device 100 may be a device that obtains a medical image and displays a medical image on a screen. For example, as shown in FIG. 1, the medical image display device 100 may be a magnetic resonance imaging device (hereinafter, referred to as a MRI device) 101, a computed tomography device (hereinafter, referred to as a CT device) 102, an X-ray device (not shown), an angiography device (not shown), an ultrasound device 103, etc. but not limited thereto.

The MRI device 101 refers to a device that obtains an image corresponding to a cross-section part of an object as strength of a magnetic resonance (MR) signal with regard to a radio frequency (RF) signal generated in a magnetic field of specific strength is represented with a contrast.

The CT device 102 has advantages of providing a cross-section image of an object and showing the internal structure (e.g. organs such as a kidney, a lung, etc.) of the object without overlapping as compared with general X-ray devices. The CT device 102 may provide a relatively accurate cross-section image with regard to an object by obtaining and processing tens or hundreds of images corresponding to a thickness of 2 mm or less per second.

The X-ray device refers to a device that emits an X-ray to a human body and obtains an image corresponding to the internal structure of the human body. The angiography device refers to a device that shows a blood vessel (e.g. arteries and veins) of a subject, into which a contrast medium is injected through a narrow tube called a catheter of about 2 mm, through an X-ray.

The ultrasound device 103 transmits an ultrasound signal from the surface of the object body toward a predetermined part in the inside of the body, and obtains an image of a blood flow or plane section of soft tissue based on information of an ultrasound signal (hereinafter, referred to as an ultrasound eco signal) reflected from the tissue inside the body.

According to one embodiment of the present disclosure, the medical image display device 100 may be materialized in various forms. For example, the medical image display device 100 to be described in this specification may be achieved in the form of a mobile terminal as well as a stationary terminal. As an example of the mobile terminal, there are a smart phone, a smart pad, a tablet personal computer (PC), a laptop computer, a personal digital assistant (PDA), etc.

According to one embodiment of the present disclosure, the medical image display device 100 may exchange medical image data with other medical devices in hospital or hospital servers connected through a picture archiving and communication system (PACS). Further, the medical image display device 100 may perform data communication with a server or the like in accordance with standards of digital imaging and communications in medicine (DICOM).

According to one embodiment of the present disclosure, the medical image display device 100 may include a touch screen. The touch screen may be configured to detect not only a touch input position and a touched area, but also a touch input pressure. Further, the touch screen may be configured to detect a proximity touch as well as a real touch.

In this specification, the real touch refers to an input caused by real contact between a screen and a user's body (e.g. a finger) or a touch pen given as a touch tool (e.g. a pointing device, a stylus, a haptic pen, an electronic pen, etc.). The proximity touch refers to an input caused by not real contact between a screen and a user's body or a touch tool but an approach up to a predetermined distance from the screen (e.g. hovering within a detectable distance of 30 mm or less).

The touch screen may be for example achieved by a resistive type, a capacitive type, an infrared type, or an acoustic wave type.

According to one embodiment of the present disclosure, the medical image display device 100 may sense a gesture input as a user's touch input to a medical image through the touch screen.

As a user's touch input to be described in this specification, there are a tap, a click stronger than the tap, touch and hold, a double tap, a double click, a drag corresponding to movement by a predetermined distance while keeping the touch, drag and drop, slide, flicking, panning, swipe, pinch, etc. The drag, slide, flicking, swipe, and the like input is divided into press corresponding to contact between the touch screen and a finger (or a touch pen), movement by a predetermined distance, and release from the touch screen, and includes all kinds of movement in the form of a straight line or a curved line. These various touch inputs are involved in the gesture input.

According to one embodiment of the present disclosure, the medical image display device 100 may provide some or all of buttons for controlling a medical image in the form a graphic user interface (GUI).

Figure 2:
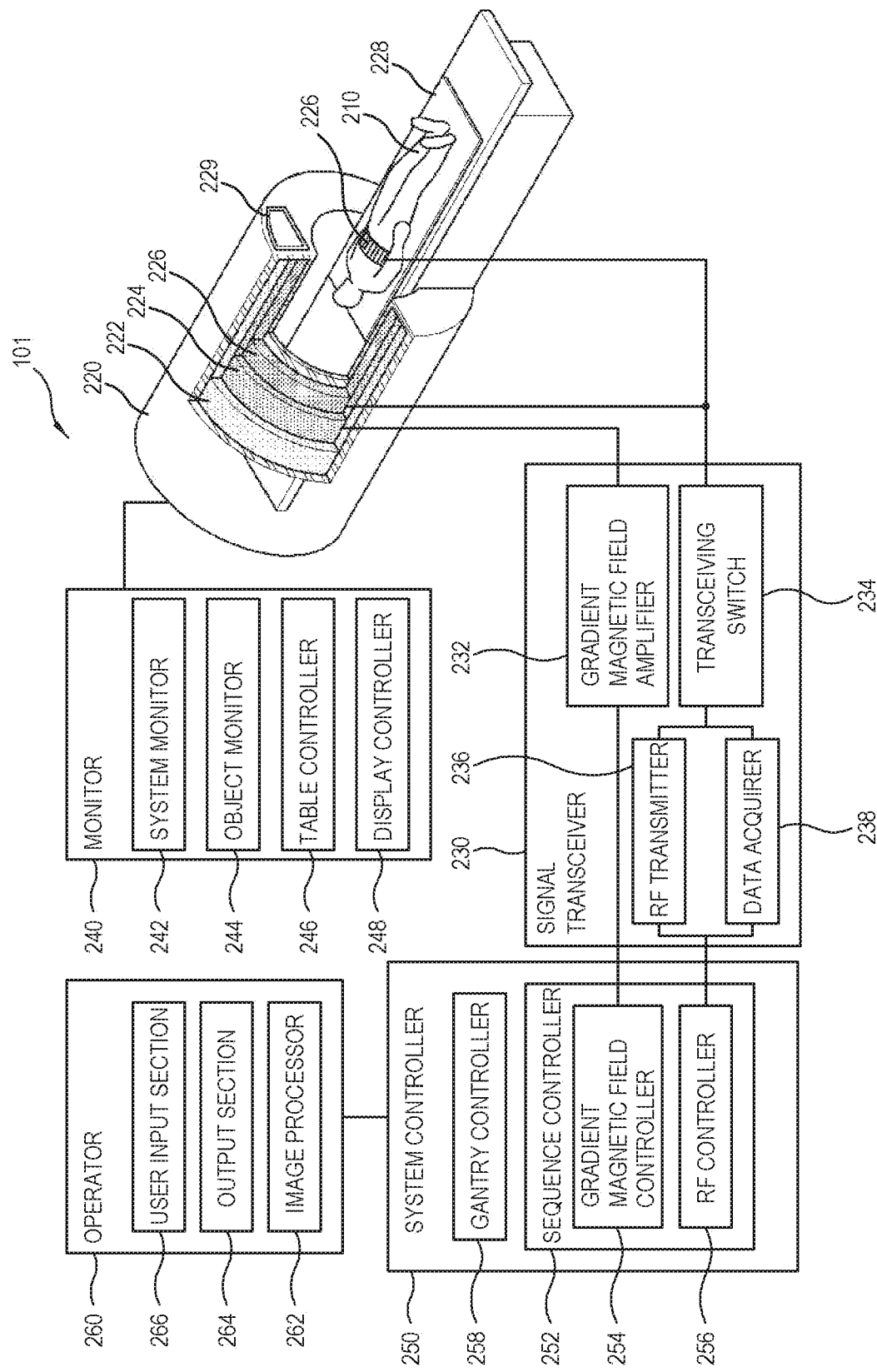
FIG. 2 is a view for schematically illustrating an MRI device according to one embodiment of the present disclosure.

FIG. 2 is a view for schematically illustrating an MRI device according to one embodiment of the present disclosure.

In this embodiment, the magnetic resonance image (MRI) indicates an image of an object, obtained using a nuclear magnetic resonance (NMR).

The MRI device 101 refers to a device for obtaining an image of a tomography part of an object by representing a contrast based on strength of a magnetic resonance (MR) signal with regard to a radio frequency (RF) signal generated in a magnetic field of specific strength. For example, an MR signal is emitted from a specific atomic nucleus when an RF signal resonating with only the specific atomic nucleus (e.g. a hydrogen nucleus) is instantaneously emitted and stopped after an object is laid within a strong magnetic field, and thus the MRI device 101 receives the MR signal and obtains an MR image. The MR signal means an RF signal emitted from an object. The strength of the MR signal may be varied depending on percentage of atoms (e.g. hydrogen or the like) included in the object, relaxation time T1, relaxation time T2, blood flow or the like flow.

The MRI device 101 has features different from the other imaging devices. Unlike the CT and the like imaging devices in which the image is obtained depending on orientation of detecting hardware, the MRI device 101 is capable of obtaining a 3D volume image or 2D image oriented toward any point. Further, unlike the CT, X-ray, PET and SPECT, the MRI device 101 makes an object and an examiner free from radiation exposure, is capable of obtaining an image with a high contrast in soft tissue and also obtaining an neurological image, an intravascular image, a musculoskeletal image, an oncologic image, and the like in which clear representation of abnormal tissue is important.

As shown in FIG. 1, the MRI device 101 in this embodiment may include a gantry 220, a signal transceiver 230, a monitor 240, a system controller 250, and an operator 260.

The gantry 220 prevents electromagnetic waves generated by a main magnet 222, a gradient coil 224, an RF coil 226, and the like from radiating outward. A static magnetic field and a gradient magnetic field is formed in a bore inside the gantry 220, and an RF signal is emitted toward an object 210.

The main magnet 222, the gradient coil 224, and the RF coil 226 may be arranged along a predetermined direction of the gantry 220. The predetermined direction may include a coaxial cylindrical direction or the like. The object 210 may be positioned on a table 228 that can be inserted in a cylinder along a horizontal axis of the cylinder.

The main magnet 222 generates the static magnetic field for making magnetic dipole moment of atomic nuclei included in the object 210 be oriented in a certain direction. The stronger and more uniform the magnetic field is caused by the main magnet, the more precise and accurate the MR image of the object 210 is obtained.

The gradient coil 224 includes X, Y, and Z coils for generating the gradient magnetic fields in X-axial, Y-axial and Z-axial directions which are orthogonal to one another. The gradient coil 224 induces resonance frequencies to be varied depending on parts of the object 210, thereby providing position information about each part of the object 210.

The RF coil 226 emits an RF signal to a patient, and receives an MR signal emitted from the patient. Specifically, the RF coil 226 transmits the RF signal having the same frequency as a precessional frequency toward the atomic nuclei having a precessional motion, and stops transmitting the RF signal to receive the MR signal emitted from the patient.

For example, the RF coil 226 may generate an electromagnetic wave signal, e.g. an RF signal, having a radio frequency corresponding to the kind of atomic nucleus for transition of a certain atomic nucleus from a low energy state to a high energy state, and apply it to the object 210. When the electromagnetic wave signal generated by the RF coil 226 is applied to a certain atomic nucleus, this atomic nucleus may be transited from the low energy state to the high energy state. Thereafter, when the electromagnetic wave generated by the RF coil 226 disappears, the atomic nucleus subjected to the electromagnetic wave is transited from the high energy state to the low energy state, and thus radiates electromagnetic waves having the Lamor frequency. In other words, when the electromagnetic wave signal being applied to the atomic nuclei is stopped, the electromagnetic wave having the Lamor frequency may be radiated while change in energy level from high energy to low energy is made in the atomic nuclei subjected to the electromagnetic wave. The RF coil 226 may receive the electromagnetic wave signal radiated from the atomic nuclei inside the object 210.

The RF coil 226 may be materialized by a single RF transceiving coil that functions not only to generate electromagnetic waves having a radio frequency corresponding to the kind of atomic nucleus, but also receive the electromagnetic waves radiated from the atomic nucleus. Alternatively, the RF coil 226 may be materialized by a transmitting RF coil functioning to generate electromagnetic waves having a radio frequency corresponding to the kind of atomic nucleus, and a receiving RF coil functioning to receive the electromagnetic waves radiated from the atomic nucleus Further, the RF coil 226 may be integrated into or detachably provided in the gantry 220. The detachable RF coil 226 may include RF coils corresponding to parts of the object, such as a head RF coil, a chest RF coil, a leg RF coil, a neck RF coil, a shoulder RF coil, a wrist RF coil, an ankle RF coil, etc.

Further, the RF coil 226 may communicate with an external device by a wire and/or wirelessly, and may perform dual-tune communication according to communication frequency bands.

Further, the RF coil 226 may include a birdcage coil, a surface coil, and a transverse electromagnetic (TEM) coil in accordance with structures of the coil.

Further, the RF coil 226 may include a transmission-dedicated coil, a reception-dedicated coil, and a transmission/reception convertible coil in accordance with RF signal transceiving methods.

Further, the RF coil 226 may include an RF coil of various channels such as 16 channels, 32 channels, 72 channels, 144 channels, etc.

Below, it will be described by way of example that the RF coil 226 is a radio frequency multi coil including N coils corresponding to a plurality of channels, e.g. the first to Nth channels. Here, the radio frequency multi coil may be also called a multi-channel RF coil.

The gantry 220 may further include a display 229 placed outside the gantry 220, and a display (not shown) placed inside the gantry 220. Through the display placed inside and/or outside the gantry 220, it is possible to provide a predetermined piece of information to a user or an object.

The signal transceiver 230 controls the gradient magnetic field formed inside, i.e. in the bore of the gantry 220 in accordance with predetermined MR sequences, and controls the RF signal and the MR signal to be transmitted and received.

The signal transceiver 230 may include a gradient magnetic field amplifier 232, a transceiving switch 234, an RF transmitter 236 and an RF data acquirer 238.

The gradient magnetic field amplifier 232 may drive the gradient coil 224 included in the gantry 220, and supply a pulse signal for generating the gradient magnetic field to the gradient coil 224 under control of a gradient magnetic field controller 254. By controlling the pulse signal supplied from the gradient magnetic field amplifier 232 to the gradient coil 224, it is possible to combine the gradient magnetic fields in X-axial, Y-axial, Z-axial directions.

The RF transmitter 236 and the RF data acquirer 238 may drive the RF coil 226. The RF transmitter 236 may supply an RF pulse having the Lamor frequency to the RF coil 226, and the RF data acquirer 238 may receive the MR signal received in the RF coil 226.

The transceiving switch 234 may adjust the direction of transceiving the RF signal and the MR signal. For example, the RF signal is transmitted to the object 210 through the RF coil 226 during a transmitting mode, and the MR signal is received from the object 210 through the RF coil 226 during a receiving mode. The transceiving switch 234 may be controlled by a control signal from the RF controller 256.

The monitor 240 may monitor or control the gantry 220 or the devices mounted to the gantry 220. The monitor 240 may include a system monitor 242, an object monitor 244, a table controller 246, and a display controller 248.

The system monitor 242 may monitor and control a state of a static magnetic field, a state of a gradient magnetic field, a state of an RF signal, a state of an RF coil, a state of a table, a state of a device for measuring body information of an object, a power supply state, a state of a heat exchanger, a state of a compressor, etc.

The object monitor 244 monitors the state of the object 210. Specifically, the object monitor 244 may include a camera for observing a motion or position of the object 210, a spirometer for measuring breathing of the object 210, an electrocardiogram (ECG) sensor for sensing an electrocardiogram of the object 210, or a thermometer for measuring a body temperature of the object 210.

The table controller 246 controls movement of a table 228 on which the object 210 lies. The table controller 246 may control the movement of the table 228 under sequence control of a sequence controller 252. For example, in case of the moving imaging of the object, the table controller 246 may move the table 228 continuously or intermittently under the sequence control of the sequence controller 252, and it is thus possible to take an image of the object in a field of view (FOV) greater than the FOV of the gantry.

The display controller 248 controls the display 229 placed outside and/or inside the gantry 220. Specifically, the display controller 248 may turn on/off the display 229 placed outside and/or inside the gantry 220, or control the screen to be output to the display 229, etc. Further, when a loudspeaker is placed inside or outside the gantry 220, the display controller 248 may turn on/off the loudspeaker, or control a sound or the like to be output through the loudspeaker.

The system controller 250 may include the sequence controller 252 for controlling sequences of signals generated inside the gantry 220, and the gantry controller 258 for controlling the gantry 220 and the devices mounted to the gantry 220.

The sequence controller 252 may include a gradient magnetic field controller 254 for controlling the gradient magnetic field amplifier 232, and the RF controller 256 for controlling the RF transmitter 236, the RF data acquirer 238 and the transceiving switch 234. The sequence controller 252 may control the gradient magnetic field amplifier 232, the RF transmitter 236, the RF data acquirer 238 and the transceiving switch 234 in accordance with pulse sequences received from the operator 260.

Herein, the pulse sequence refers to a sequence of signals repetitively applied by the MRI device 101. The pulse sequence may include time parameters of an RF pulse, for example, repetition time (TR), time to an echo (TE), etc.

In this embodiment, the pulse sequence includes all kinds of information needed for controlling the gradient magnetic field amplifier 232, the RF transmitter 236, the RF data acquirer 238, and the transceiving switch 234, and may for example include intensity of a pulse signal applied to the gradient coil 224, applying time, applying timing, etc.

The operator 260 gives pulse sequence information to the system controller 250, and at the same time controls general operations of the MRI device 101.

The operator 260 may include an image processor 262 for processing the MR signal received from the RF data acquirer 238, an output section 264, and a user input section 266.

The image processor 262 processes the MR signal received from the RF data acquirer 238 to generate an MR image data about the object 210.

The image processor 262 performs various signal processes such as amplification, frequency conversion, phase detection, low-frequency amplification, filtering, etc. with regard to the MR signal received in the RF data acquirer 238.

The image processor 262 may for example arrange digital data in a k space of a memory, and apply the 2D or 3D Fourier transformation to the data to thereby reconstruct image data.

Further, the image processor 262 may perform a synthesis process, a differential operation process, etc. with regard to image data as necessary. The synthesis process may include a pixel additive process, a maximal intensity projection (MIP) process, etc. Further, the image processor 262 may process not only the image data subjected to the reconstruction but also the image data subjected to the synthesis process or the differential operation process to be stored in a memory (not shown) or an external server.

Further, various signal processes applied by the image processor 262 to the MR signal may be performed in parallel. For example, the plurality of MR signals received in the multi-channel RF coil are subjected to signal processes in parallel, thereby constructing the image data with the plurality of MR signals.

The output section 264 may output the image data generated or reconstructed by the image processor 262 to a user. Further, the output section 264 may output a user interface (UI), user information, object information and the like information needed for a user to control the MRI system.

The output section 264 may include a loudspeaker, a printer, a display, etc. There are no limits to the materialization of the display, and the display may be materialized by various display types, for example, liquid crystal, plasma, a light-emitting diode, an organic light-emitting diode, a surface-conduction electron-emitter, a carbon nano-tube, nano-crystal, etc. Further, the display may be materialized to display an image in a 3D form, or may be materialized by a transparent display as necessary.

In this embodiment, the output section 264 may include various output devices without departing from the scope obvious to those skilled in the art.

Through the user input section 266 a user may input object information, parameter information, a scan condition, a pulse sequence, information about image synthesis or differential operation, etc. The user input section 266 may include a keyboard, a mouse, a trackball, a voice recognizer, a gesture recognizer, a touch pad, etc. and may include various input devices without departing from the scope obvious to those skilled in the art.

FIG. 2 shows the signal transceiver 230, the monitor 240, the system controller 250 and the operator 260 as elements separated from one another, but it will be understood by those skilled in the art that the functions respectively performed in the signal transceiver 230, the monitor 240, the system controller 250 and the operator 260 may be performed in other elements. For example, the image processor 262 converts the MR signal received in the RF data acquirer 238 into a digital signal, but this conversion into the digital signal may be directly performed by the RF data acquirer 238 or the RF coil 226.

The gantry 220, the RF coil 226, the signal transceiver 230, the monitor 240, the system controller 250 and the operator 260 may be connected to one another wirelessly or by a wire. When they are connected wirelessly, a device (not shown) for synchronizing clocks therebetween may be additionally provided. Communication between the gantry 220, the RF coil 226, the signal transceiver 230, the monitor 240, the system controller 250 and the operator 260 may be performed using a low voltage differential signaling (LVDS) or the like high-speed digital interface, a universal asynchronous receiver transmitter (UART) or the like asynchronous serial communication, an error synchronous serial communication, a controller area network (CAN) or the like low-delay network protocol, optical communication, etc., and may be performed using various communication methods without departing from the scope obvious to those skilled in the art.

Figure 3:
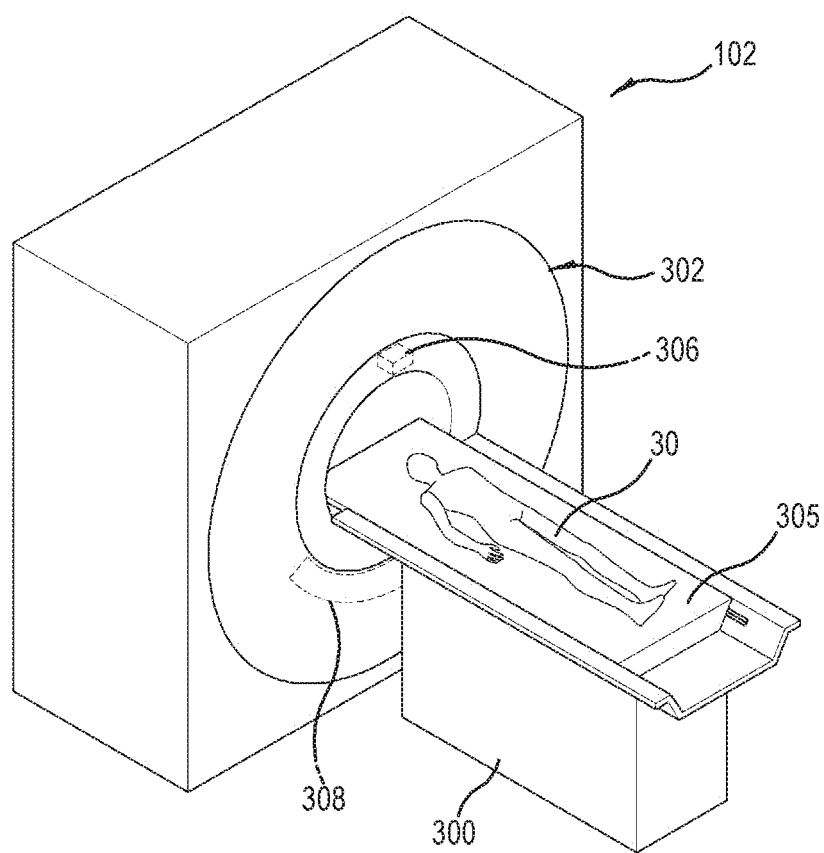
FIG. 3 is a view for illustrating a CT device according to one embodiment of the present disclosure.
Figure 4:
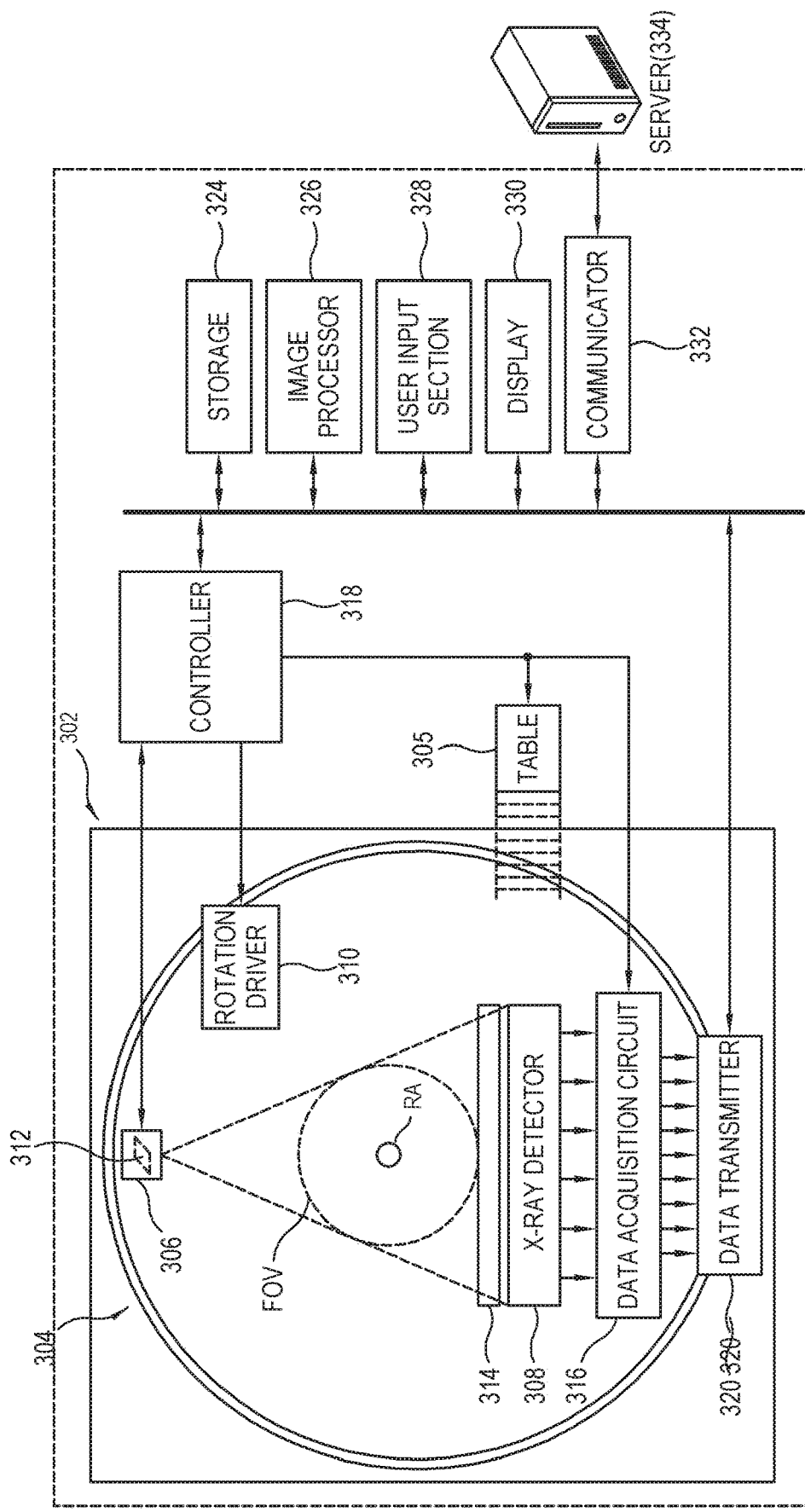
FIG. 4 is a view for schematically illustrating a configuration of the CT device of FIG. 3.

FIG. 3 is a view for illustrating a CT device 102 according to one embodiment of the present disclosure, and FIG. 4 is a view for schematically illustrating a configuration of the CT device 102 of FIG. 3.

As shown in FIG. 3, the CT device 102 may include a gantry 302, a table 305, an X-ray generator 306, and an X-ray detector 308.

Since the CT device 102 and the like tomography device can provide a cross-section image of the object, it is advantageous to show the internal structure (e.g. organs such as a kidney, a lung, etc.) of the object without overlapping as compared with general X-ray devices.

The tomography device may include all kinds of tomography device such as the CT device, an optical coherence tomography (OCT) device, a positron emission tomography (PET)-CT device, and the like.

In this embodiment, the tomography image is an image obtained by applying tomography to an object in the tomography device, and may indicate an image obtained by using data projected after emitting an X-ray or the like beam to an object. Specifically, the CT image may refer to an image obtained by synthesizing a plurality of X-ray images obtained by photographing the object while rotating with respect to at least one axis of the object.

Below, as a tomography device 300, the CT device 102 shown in FIG. 2 and FIG. 3 will be described by way of example.

The CT device 102 may provide a relatively accurate cross-section image with regard to an object by obtaining and processing tens or hundreds of images corresponding to a thickness of 2 mm or less per second. There is a conventional problem of showing only the transverse cross-section of the object, but this problem has been overcome by various image reconstruction techniques as follows. There are the imaging techniques for 3D reconstruction as follows.

Shade surface display (SSD): The early 3D imaging technique in which only voxels having a certain HU values are represented.

Maximum intensity projection (MIP)/minimum intensity projection (MinIP): The 3D technique of showing only voxels having the highest or lowest HU value among the voxels of forming the image.

Volume rendering (VR): The technique for adjusting color and penetrance of the voxels of forming the image according to interesting regions.

Virtual endoscopy: The technique in which a 3D image reconstructed by the VR or SSD technique is observed through endoscopy.

Multi planar reformation (MPR): The imaging technique for reconstruction with different cross-section images. The reconstruction is possible in a direction as desired by a user.

Editing: Various techniques for arranging surrounding voxels to more easily observe an interesting portion in the VR.

Voxel of interest (VOI): Technique for representing only a selected region with the VR.

The CT device 102 according to one embodiment of the present disclosure will be described with reference to FIG. 3 and FIG. 4. The CT device 102 according to one embodiment of the present disclosure may include various devices as shown in FIG. 4.

The gantry 302 may include the X-ray generator 306 and the X-ray detector 308.

An object 30 may lie on the table 305.

During a CT process, the table 305 may move in a predetermined direction (for example, at least one of up, down, left and right directions). Further, the table 305 may be tilted or rotated at a predetermined angle in a predetermined direction.

Further, the gantry 302 may be tilted at a predetermined angle in a predetermined direction.

As shown in FIG. 4, The CT device 102 according to one embodiment of the present disclosure may include the gantry 302, the table 305, the controller 318, a storage 324, an image processor 326, a user input section 328, a display 330, and a communicator 332.

As described above, the object 310 may lie on the table 305. The table 305 according to one embodiment of the present disclosure can move in a predetermined direction (for example, at least one of up, down, left and right directions), and may be controlled to move by the controller 318.

The gantry 302 according to one embodiment of the present disclosure may include a rotary frame 304, the X-ray generator 306, the X-ray detector 308, a rotation driver 310, a data acquisition circuit 316, and a data transmitter 320.

The gantry 302 according to one embodiment of the present disclosure may include the rotary frame 304 having a ring shape, which can be rotated with respect to a predetermined rotation axis (RA). Further, the rotary frame 304 may be shaped like a disc.

The rotary frame 304 may include the X-ray generator 306 and the X-ray detector 308, which are arranged to have a predetermined field of view (FOV). Further, the rotary frame 304 may include an anti-scatter grid 314. The anti-scatter grid 314 may be placed between the X-ray generator 306 and the X-ray detector 308.

In the medical image display device, X-ray radiation, which reaches a detector (or a photosensitive film), may include not only attenuated primary radiation of forming a useful image but also scattered radiation or the like of deteriorating the quality of the image. To transmit most of primary radiation and attenuate the scattered radiation, the anti-scatter grid 314 may be arranged between a patient and the detector (or the photosensitive film).

For example, the anti-scatter grid may be structured by alternately stacking interspace materials such as strips of lead foil and a solid polymer material or a solid polymer and a fiber composite material. However, there are no limits to the foregoing structure of the anti-scatter grid.

The rotary frame 304 may rotate the X-ray generator 306 and the X-ray detector 308 at a predetermined rotating speed based on a driving signal received from the rotation driver 310. The rotary frame 304 may receive a driving signal and power from the rotation driver 310 by a contact method using a slip ring. Further, the rotary frame 304 may receive a driving signal and power from the rotation driver 310 through wireless communication.

The X-ray generator 306 receives voltage and current through a high-voltage generator (not shown) via the slip ring (not shown) from a power distribution unit (PDU, not shown) and generates and emits an X-ray. When the high-voltage generator applies a predetermined voltage (hereinafter, referred to as a tube voltage), the X-ray generator 306 can generate X-rays having a plurality of energy spectra corresponding to such a predetermined tube voltage.

The X-ray generated by the X-ray generator 306 may be emitted in a predetermined form by a collimator 112.

The X-ray detector 308 may be placed facing the X-ray generator 306. The X-ray detector 308 may include a plurality of X-ray detecting elements. The single X-ray detecting element may form a single channel, but is not limited thereto.

The X-ray detector 308 senses the X-ray generated by the X-ray generator 306 and received via the object 30, and generates an electric signal corresponding to the intensity of the sensed X-ray.

The X-ray detector 308 may include an indirect detector that detects light converted from radiation, and a direct detector that detects electric charges converted from the radiation. The indirect X-ray detector may employ a scintillator. Further, the direct X-ray detector may employ a photon counting detector. The data acquisition system (DAS) 316 may be connected to the X-ray detector 308. The electric signal generated by the X-ray detector 308 may be collected in the DAS 316. The electric signal generated by the X-ray detector 308 may be collected in the DAS 316 by a wire or wirelessly. Further, the electric signal generated by the X-ray detector 308 may be provided to an analog/digital converter (not shown) via an amplifier (not shown).

Only some pieces of data collected from the X-ray detector 308 may be provided to the image processor 326 in accordance with slice thickness or the number of slices, or the image processor 326 may select only some pieces of data.

Such a digital signal may be provided to the image processor 326 through the data transmitter 320. The digital signal may be transmitted to the image processor 326 via the data transmitter 320 by a wire or wirelessly.

The controller 318 of the CT device 102 according to one embodiment of the present disclosure may control operations of modules in the CT device 102. For example, the controller 318 may control the operations of the table 305, the rotation driver 310, the collimator 312, the DAS 316, the storage 324, the image processor 326, the user input section 328, the display 330, the communicator 332, etc.

The image processor 326 receives data (e.g. pure data before process) acquired from the DAS 316 through the data transmitter 320, and performs a pre-processing process.

The pre-processing process may for example include a correction process for sensitivity inhomogeneity between channels, a correction process for signal loss due to sudden decrease in signal strength or an X-ray absorbing material such as metal, etc.

The output data of the image processor 326 may be called raw data or projection data. The projection data may be stored together with image-taking conditions (e.g. a tube voltage, an image-taking angle, etc.) for obtaining data in the storage 324.

The projection data may be a set of data values corresponding to the intensity of the X-ray passed through the object. For convenience of description, a set of projection data simultaneously obtained at the same image-taking angle with regard to all channels will be called a projection data set.

The storage 324 may include at least one type of storage media such as a flash memory type, a hard disk type, a multimedia card micro type, a card type memory (an SD, XD and the like memories), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disc.

Further, the image processor 326 may use the acquired projection data set to reconstruct a cross-section image of an image. The cross-section image may be a 3D image. In other words, the image processor 326 may generate a 3D image of the object by using a cone beam reconstruction method or the like based on the acquired projection data set.

Through the user input section 328, an external input about an X-ray tomography condition, an image processing condition, etc. may be received. For example, the X-ray tomography condition may include a plurality of tube voltages, energy level settings for a plurality of X-rays, selection of a tomography protocol, selection of the image reconstruction method, settings for an FOV region, the number of slices, slice thickness, settings for image post-processing parameters, etc. Further, the image processing condition may include a resolution of an image, attenuation coefficient settings for the image, combination ratio settings for the image, etc.

The user input section 328 may include a device or the like for receiving a predetermined input from the outside. For example, the user input section 328 may include a microphone, a keyboard, a mouse, a joystick, a touch pad, a touch pen, voice and gesture recognition devices, etc.

The display 330 may display an X-ray tomography image reconstructed by the image processor 326.

The data, power, etc. may be transceived between the foregoing elements by at least one of wired, wireless and optical communications.

The communicator 332 may communicate with an external device, an external medical device, etc. through a server 334.

Figure 5:
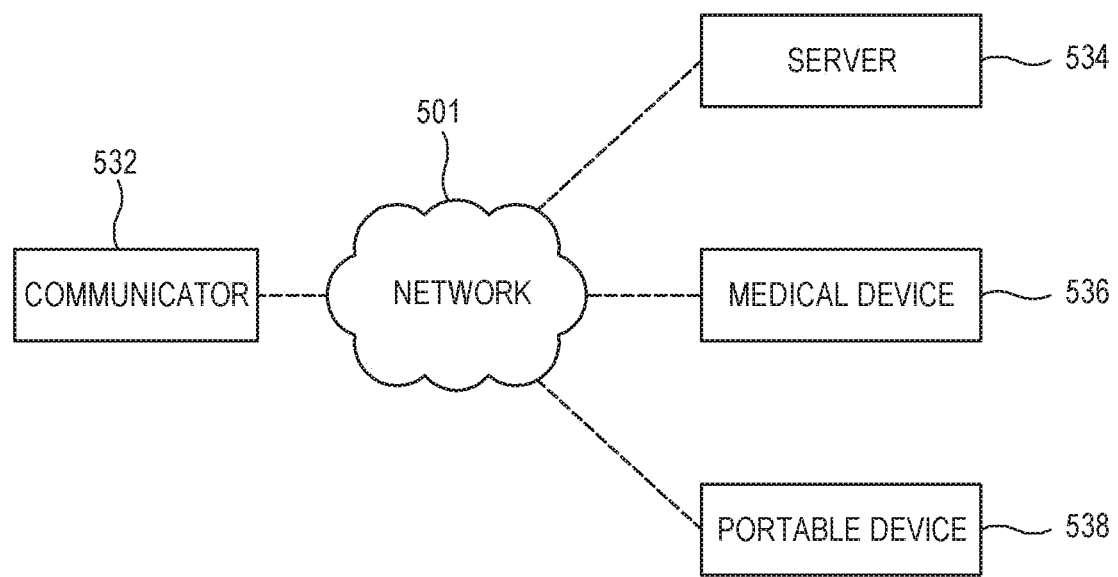
FIG. 5 is a view for schematically illustrating a configuration of a communicator for communicating with the outside in a network system.

FIG. 5 is a view for schematically illustrating a configuration of a communicator 532 for communicating with the outside in a network system, The communicator 532 shown in FIG. 5 may connect with at least one among the gantry 220, the signal transceiver 230, the monitor 240, the system controller 250 and the operator 260 shown in FIG. 2. That is, the communicator 532 may exchange data with a hospital server connected via the picture archiving and communication system (PACS) or other medical devices in the hospital, and may perform data communication in accordance with standards of the digital imaging and communications in medicine (DICOM).

As shown in FIG. 5, the communicator 532 connects with a wire or wireless network 501 and performs communication with an external server 534, an external medical device 536, or a portable device and the like external device 538.

Specifically, the communicator 532 may transmit and receive data related to diagnosis of an object through the network 501, and may also transmit and receive an medical image taken by the CT, ultrasound, X-ray and the like other medical devices 536.

According to one embodiment of the present disclosure, the communicator 532 shown in FIG. 5 may be included in the CD device 102 of FIG. 4. In this case, the communicator 532 shown in FIG. 4 is equivalent to the communicator 332 shown in FIG. 3. Further, other medical devices 536 may be for example the MRI device 101 or the ultrasound device 103 shown in FIG. 1.

Further, the communicator 532 shown in FIG. 5 may be included in the MRI device 101 of FIG. 2. In this case, the MRI device 101 shown in FIG. 2 may further include the communicator 532 of FIG. 5. Further, other medical devices 536 may be for example the CT device 102 or the ultrasound device 103 shown in FIG. 1.

Detailed operations of the communicator 532 are as follows.

The communicator 532 may connect with the wired or wireless network 501 and perform communication with a server 534, an external medical device 536 or an external device 538. The communicator 532 may exchange data with a hospital server connected through the PACS or other medical devices in the hospital.

Further, the communicator 532 may perform data communication with the external device 538 or the like in accordance with the DICOM standards.

The communicator 532 may transmit and receive an image of an object and/or data related to diagnosis of the object through a network 501. The communicator 532 may receive the medical image or the like obtained in the MRI device 101, the X-ray device, and the like other medical devices 536.

Besides, the communicator 532 may receive a diagnosis history, a care schedule, etc. of a patient from the server 534, and utilize them in a patient's clinic diagnosis or the like. Further, the communicator 532 may perform data communication with not only the server 534 or the medical devices 536 in the hospital, but also a portable device (terminal) 538 of a user or patient.

Further, defects in equipment and quality control information are transmitted to a system administrator or service representative though the network, and get a feedback on them.

As described above, the medical images obtained by various medical image display devices show the object in various ways in accordance with the kinds and image-taking methods of medical image display device. Further, the features of the obtained medical image are varied depending on the image-taking methods and kinds of medical image display device. For example, a certain medical image makes it easy to grasp cancer tissues, and another medical image makes it easy to grasp a blood vessel.

Therefore, there is a need of providing a device that gives a medical image suitable for a user's intention by taking a reading portion on an image into account.

Below, the medical image display devices according to one or other embodiments of the present disclosure, which can provide a medical image for facilitating a user's diagnosis with regard to a predetermined region in the medical image, will be described in detail with reference to the accompanying drawings.

The medical image display devices according to one or other embodiments of the present disclosure may include any image processing device capable of displaying, storing and/or processing the medical image.

Specifically, the medical image display device 100 according to one or other embodiments of the present disclosure may be involved in the tomography device such as the MRI device 101, the CT device 102 or the like described with reference to FIG. 2 to FIG. 4. In this case, the medical image display device 100 may include the communicator 532 described with reference to FIG. 5.

Further, the medical image display device 100 according to one or other embodiments of the present disclosure may be involved in the server 534, the medical device 536 or the external device, i.e. the portable terminal 538 connecting through the network 501 with at least one of the tomography devices such as the MRI device 101 and the CT device 102 described with reference to FIG. 2 to FIG. 4. Here, the server 534, the medical device 536 or the portable terminal 538 may be an image processing device capable of displaying, storing or processing at least one of the MRI image and the tomography image. For example, the medical image display device according to one or other embodiments of the present disclosure may be given in the form of the server 534, the medical device 536 or the portable terminal 538, and may be the PACS capable for displaying, storing or processing at least one of the MRI image and the tomography the image.

Further, the medical image display device 100 according to one or other embodiments of the present disclosure may be involved in any medical image device/system for processing/recovering an image based on data obtained by scanning an object, besides the MRI device 101 or the CT device 102, or may be connected to any medical image device/system.

The medical image display device 100 according to one or other embodiments of the present disclosure may be materialized by a medical image registration device that obtains a first medical image and a second medical image from two or more different medical devices, e.g. a first medical device and a second medical device, and displays an image (i.e. a third medical image) where the first medical image and the second medical image are matched.

Figure 6:
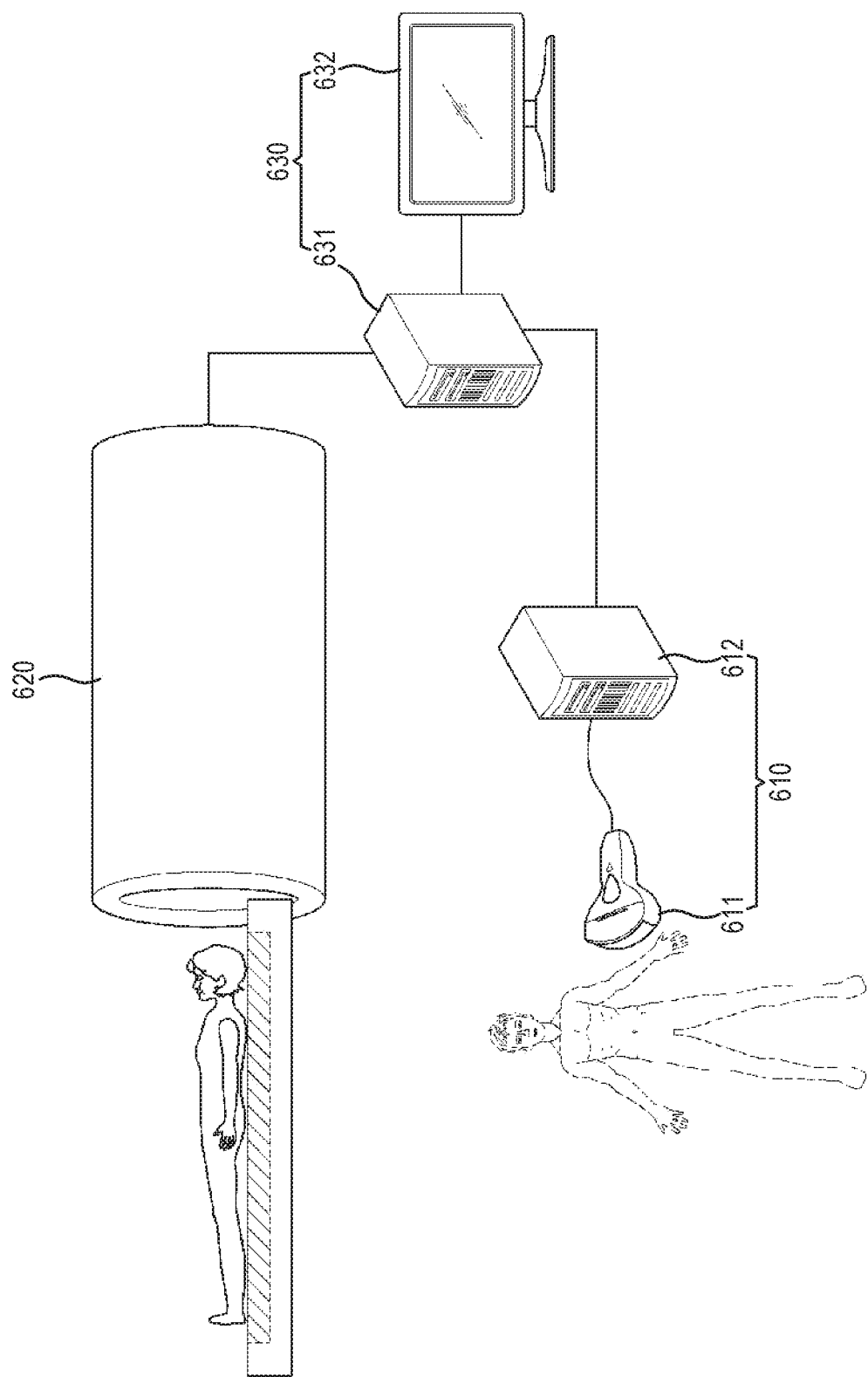
FIG. 6 is a view for illustrating a system that includes a first medical device, a second medical device, and a medical image registration device according to one embodiment of the present disclosure.

FIG. 6 is a view for illustrating a system that includes a first medical device 610, a second medical device 620, and a medical image registration device 630 according to one embodiment of the present disclosure, The first medical device 610 and the second medical device 620 respectively generates the first medical image and the second medical image, and provide them to the medical image registration device 630. The first medical image and the second medical image may be images generated by the same principle.

Further, the first medical image and the second medical image may be different in image modality. That is, the first medical image and the second medical image may be different in generation method and principle.

The medical image registration device 630 acquires the first medical image and the second medical image, and matches the first medical image and the second medical image. The images matched by the medical image registration device 630 are displayed through a display 632.

In one embodiment of the present disclosure shown in FIG. 6, the first medical device 610, the second medical device 620, and the medical image registration device 630 are materialized as devices independently of one another. Alternatively, the first medical device 610 and the medical image registration device 630 may be materialized as a single device, or the second medical device 620 and the medical image registration device 630 may be materialized as a single device. Further, the medical image registration device 630 is illustrated as including a main body 631 and the display 632. Alternatively, a separate display device for receiving and displaying image data from the medical image registration device 630 may be additionally involved in the system.

That is, the medical image registration device 630 in this embodiment may be materialized by a computer system included in another medical device capable of communicating with at least one medical device and including the display, or may be materialized by a computer system capable of communicating with two or more medical devices and including the display and the main body.

In one embodiment, the first medical device 610 may provide the first medical image in real time with regard to an interesting volume of an object. For example, when an organ is changed in shape and position as the object does physical activities, the first medial image is changed in real time.

That is, according to one embodiment of the present disclosure shown in FIG. 6, the first medical device 620 may be achieved by the ultrasound device (or ultrasonography machine) (see '103' in FIG. 1) that generates an image in real time during an interventional procedure for a patient. For example, when an organ is changed in shape and position as the object does physical activities, the medial image displayed on the display is changed in real time. However, the first medical device 620 may be another medical device such as an OCT or the like that provides an image in real time.

The first medical device 610 including the ultrasound device employs a probe 611 to apply an ultrasound signal to an interesting region of an object, and detects a reflected ultrasound signal, i.e. an ultrasound echo signal, thereby generating an ultrasound image.

The probe 611 is a part to be in contact with the object, which may include a plurality of transducer elements (hereinafter, referred to as a transducer) (not shown) and a light source (not shown). When ultrasound having several to hundreds of MHz is applied from the probe 611 to a specific part of a patient's body, this ultrasound is partially reflected from layers between many other tissues. The ultrasound is reflected from anatomical entities, which is change in density in the body, for example, blood cells in blood plasma, small structures in organs, etc.

As an example of the transducer, there may be used various kinds of ultrasound transducer such as a magnetostrictive ultrasonic transducer using a magnetostrictive effect of a magnetic body, a piezoelectric ultrasonic transducer 118 using a piezoelectric effect of a piezoelectric material, a capacitive micromachined ultrasonic transducer (cMUT) using vibration of hundreds or thousands of micromachined thin films to transmit and receive ultrasound, etc.

The plurality of transducer elements may be arranged in a linear array or convex array. Such a transducer element may be provided with a top cover for covering the plurality of transducer elements.

The light source is to emit light to the inside of the object. For example, at least one light source for emitting light having a specific wavelength may be used as the light source. Alternatively, a plurality of light sources for emitting light having different wavelengths may be used as the light source. The wavelength of the light emitted from the light source may be selected in consideration of a target inside the object. Such a light source may be materialized by a semiconductor laser (LD), a light emitting diode (LED), a solid laser, a gas laser, an optical fiber, or combination thereof.

The transducer provided in the probe 611 generates an ultrasound signal in response to a control signal, and emits the generated ultrasound signal to the object. Then, the ultrasound echo signal reflected from a specific organ (e.g. lesion) inside the object is received, i.e. detected.

Such a reflected ultrasound vibrates the transducer of the probe 611, and the transducer outputs electrical pulses corresponding to the vibration. The electric pulses are converted into an image. When the anatomical entities are different in properties of reflecting the ultrasound, for example, in an ultrasound image of a brightness (B) mode, the anatomical entities are displayed to be different in brightness.

The kinds of ultrasound image is assorted into a brightness mode (or B mode) image in which the strength of the ultrasound echo signal reflected from the object is represented with the brightness, a Doppler mode (or D mode or PW-Doppler mode) image in which an image of a moving object is represented in a spectrum form using the Doppler effect, a motion mode (or M mode) image in which a motion of an object is represented at a certain position as time goes on, an elastic mode image in which a difference between when an object is pressed or when the object is not pressed is represented on an image, a color mode image in which a speed of a moving object is represented with color using the Doppler effect, etc. The Doppler image may include not only a Doppler image corresponding to a still image, but also a Doppler image corresponding to a moving image and the like successive images. Further, the Doppler image may include both a Doppler image (2D Doppler) for a plane, and a Doppler image (3D Doppler) for a cubic space. Further, the Doppler image may include a blood flow Doppler image (or called a color Doppler image) showing a flow of blood, and a tissue Doppler image showing movement of tissue. Further, in case of the 3D image, volume data is generated from a signal received from the probe head 611, and then subjected to volume rendering, thereby generating a 3D ultrasound image.

In one embodiment, the first medical device 610 includes the probe 611, and an image processing device 612 for processing an image based on an ultrasound echo signal detected in the probe 611. The image processing device 612 may support a plurality of modes, and include image processors for generating the ultrasound images corresponding to the modes, respectively. FIG. 6 shows an example that the image processing device 612 is a computer main body and is connected to a stationary terminal, i.e. the probe 611 by a wire. The image processing device 612 may further include a display for displaying the ultrasound image.

Alternatively, the probe 611 may be achieved by not the stationary terminal, but a mobile terminal (i.e. portable terminal) that can be carried by a user and move from place to place. When the probe 611 is materialized by the mobile terminal, the probe 611 may perform wireless communication with the image processing device 612. Here, the wireless communication may include at least one of various wireless communication modules such as a short-range communication with a predetermined frequency, Wi-Fi, Wi-Fi Direct, ultra-wideband (UWB), Bluetooth, radio frequency (RF), Zigbee, wireless local area network (LAN), near field communication (NFC), etc. As an example of the image processing device 612 for processing the ultrasound image to be generated based on the ultrasound echo signal received from the probe 611, there may be a smart phone, a smart pad such as a tablet computer, a smart TV, a desktop computer, a laptop computer, a personal digital assistant (PDA), a personal portable information terminal, etc.

Alternatively, the probe 611 may be internally provided with an image processor for generating ultrasound images corresponding to the plurality of modes, and the image processing device 612 may receive an image generated in the probe 611 by a wire or wirelessly and display the image on the display.

The second medical device 620 may generate a second medical image corresponding to a volume of interest (VOI) of an object in non-real time. The second medical device 620 has a characteristic of non-real time as compared with the first medical device 610, and provides the second medical image previously generated before the medical procedure to the medical image registration device 630.

In this embodiment, the second medical device 620 may be the CT device 102 or the MRI device 101 described with reference to FIG. 2 to FIG. 4. The second medical device 620 may be materialized by an X-ray device, a single photon emission computed tomography (SPECT) device, a positron emission tomography (PET) device, etc.

In the following embodiments, it will be assumed that the second medical image is an MR or CT image for convenience of description, but the scope of the present disclosure is not limited thereto.

The medical images taken by the first medical device 610 or the second medical device 620 may be a 3D image generated by an aggregate of 2D cross-section images. For example, the second medical device 620 takes a plurality of cross-section images while changing the location and orientation of the cross-section image. When the cross-section images are aggregated, 3D volume image data may be generated to three-dimensionally show a specific part of a patient body. Like this, a method of generating the 3D volume image data based on the aggregate of the cross-section images is called multiplanar reconstruction (MPR). Similarly, the first medical device 610 may generate the 3D volume image data by hand-sweeping the probe 611, a Wabbler method, or a 3D Array probe 621.

FIG. 6 shows the case where the first medical image and the second medical image are respectively generated by different kinds of medical devices. However, according to the present disclosure, the first medical image and the second medical image may be generated by the same kind of medical device, for example, taken by one CT device 102 at different points of time.

In the following medical image display device according to one embodiment of the present disclosure, it will be assumed that the first medical image is a non-contrast medical image taken without using a contrast medium, and the second medical image is a contrast-enhanced image taken using the contrast medium.

The contrast medium injected to a patient has a problem of causing various side effects. For example, a patient may lightly feel a numbed or burning body, get hives, itchy, vomit, nausea, rashes, etc. and seriously die.

In particular, the contrast medium is not used for patients whose kidneys function poorly, unless absolutely compelled. In case of a patient who needs long-term care, a problem of costs due to use of the contrast medium cannot be ignored.

To minimize the side effects of the contrast medium, the non-contrast image is generally used in case of follow-up examination of lung cancer and lung-lesion simple diagnosis (bronchial disease, pulmonary emphysema, etc.). Specifically, based on the principle of as low as reasonably achievable (ALARA) (i.e. advice to minimize a dose and contrast medium use by international regulation), and national comprehensive cancer network (NCCN) guideline, 80% or more diagnoses have been made with the non-contrast image.

Figure 7:
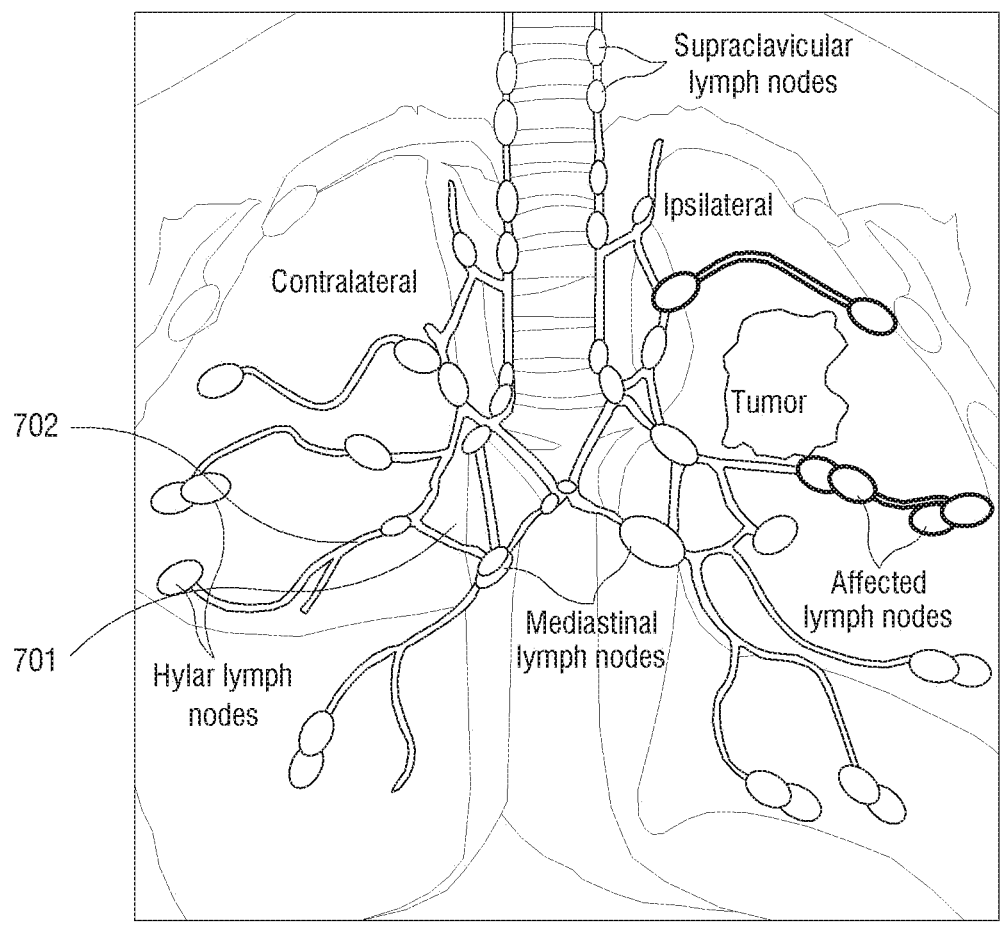
FIG. 7 is a view for conceptually illustrating a distribution of lymph nodes and blood vessels in a chest region.
Figure 8:
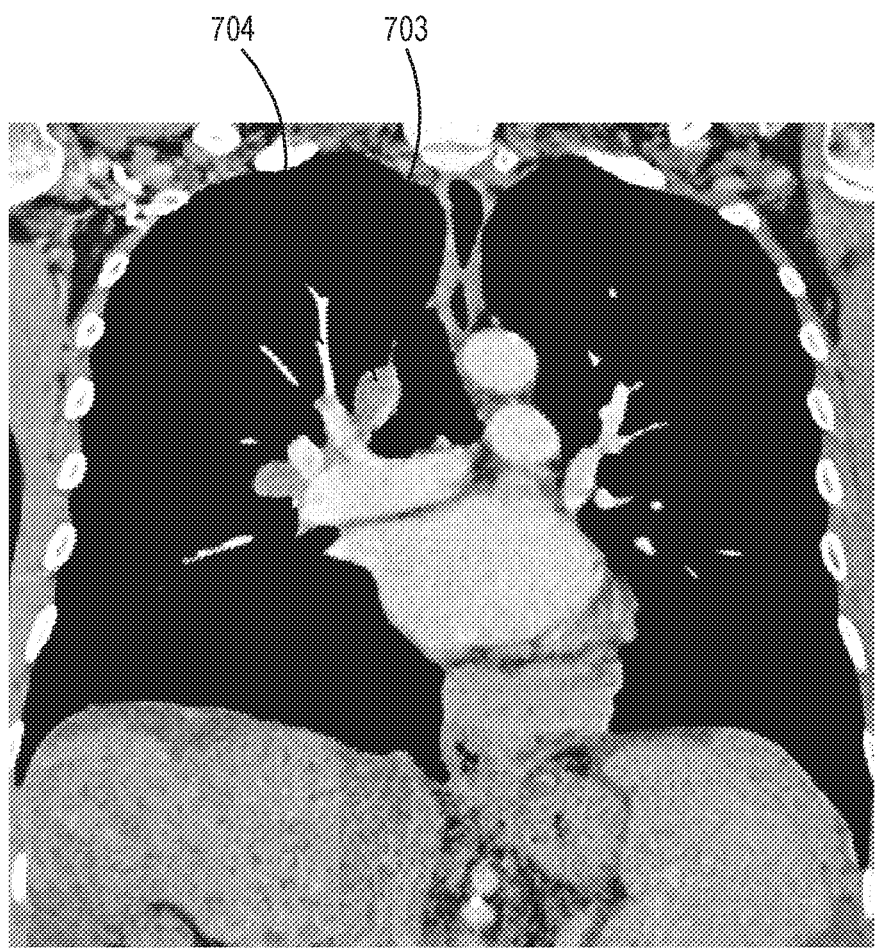
FIG. 8 is a view for illustrating a contrast-enhanced CT image obtained with regard to the chest region.
Figure 9:
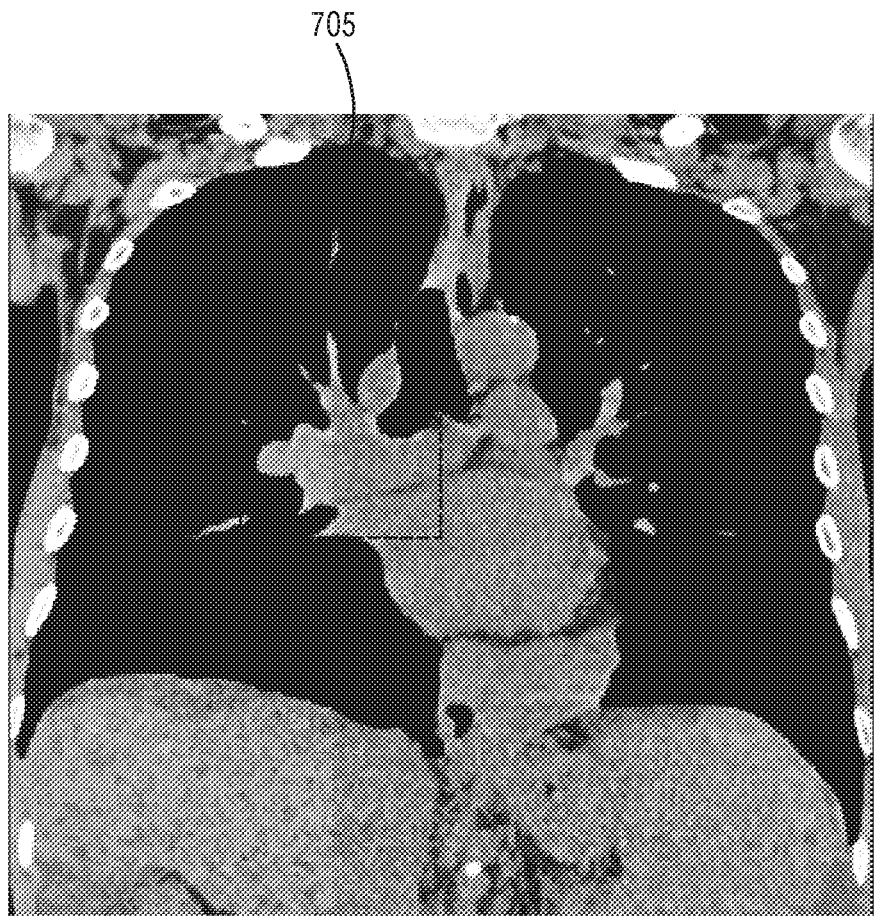
FIG. 9 is a view for illustrating a non-contrast CT image obtained with regard to the chest region.

FIG. 7 is a view for conceptually illustrating a distribution of lymph nodes and blood vessels in a chest region, FIG. 8 is a view for illustrating a contrast-enhanced CT image obtained with regard to the chest region, and FIG. 9 is a view for illustrating a non-contrast CT image obtained with regard to the chest region.

A lymph node (or lymph gland) 701 shown in FIG. 7 recognize a pathogen (e.g. an infection, a cancer cell, etc.) in a human body, and is concerned in making an immune reaction. Therefore, a degree of change in size of the lymph node, and change in the number and distribution of changed lymph nodes are important clinic decision factors in monitoring diagnosis and care.

For example, growth or metastasis of a cancer cell increases the size of the lymph node, and therefore the contrast-enhanced image may be advantageous to detect and diagnose the lymph node since it makes it easy to distinguish from other structures, in particular, a blood vessel 702.

As shown in FIG. 8, in a contrast-enhanced CT image taken by injecting the contrast medium to a patient, a lymph node 703 and a pulmonary vascular 704 are distinctively displayed. On the other hand, in a non-contrast CT image of FIG. 9, it is not easy to distinguish between the lymph node and the blood vessel in a region 705 where the lymph node is positioned.

However, the use of the contrast medium has been gradually restricted because of various side effects as described above. In a particular case of a patient who has a kidney disease, it is impossible to inject the contrast medium to him/her, and a diagnosis has been made unavoidably based on the non-contrast medical image.

Accordingly, even though the lymph-node region information is a landmark important for a lung cancer diagnosis (with regard to metastasis, state change, etc.) and a lung lesion diagnosis, the non-contrast image makes it difficult to distinguish the lymph node/blood vessel regions, thereby missing an early diagnosis of lymph-node related diseases or missing chances to cure the patient.

Figure 10:
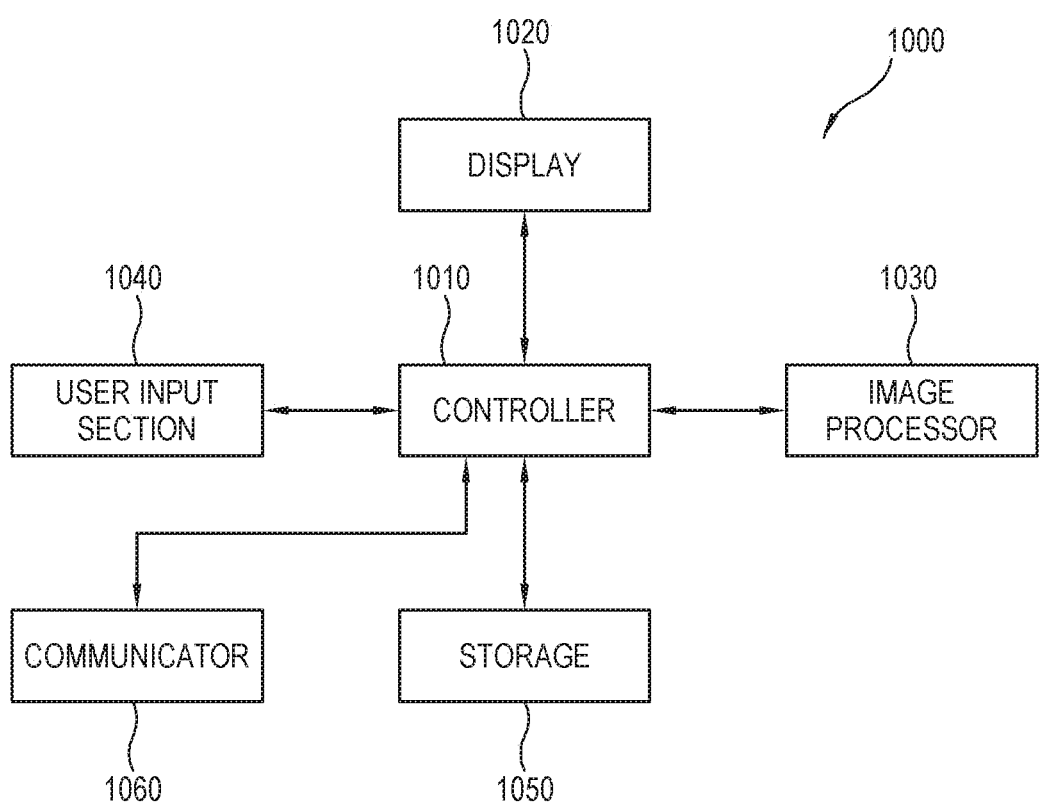
FIG. 10 is a block diagram for illustrating elements of the medical image display device according to one embodiment of the present disclosure
Figure 11:
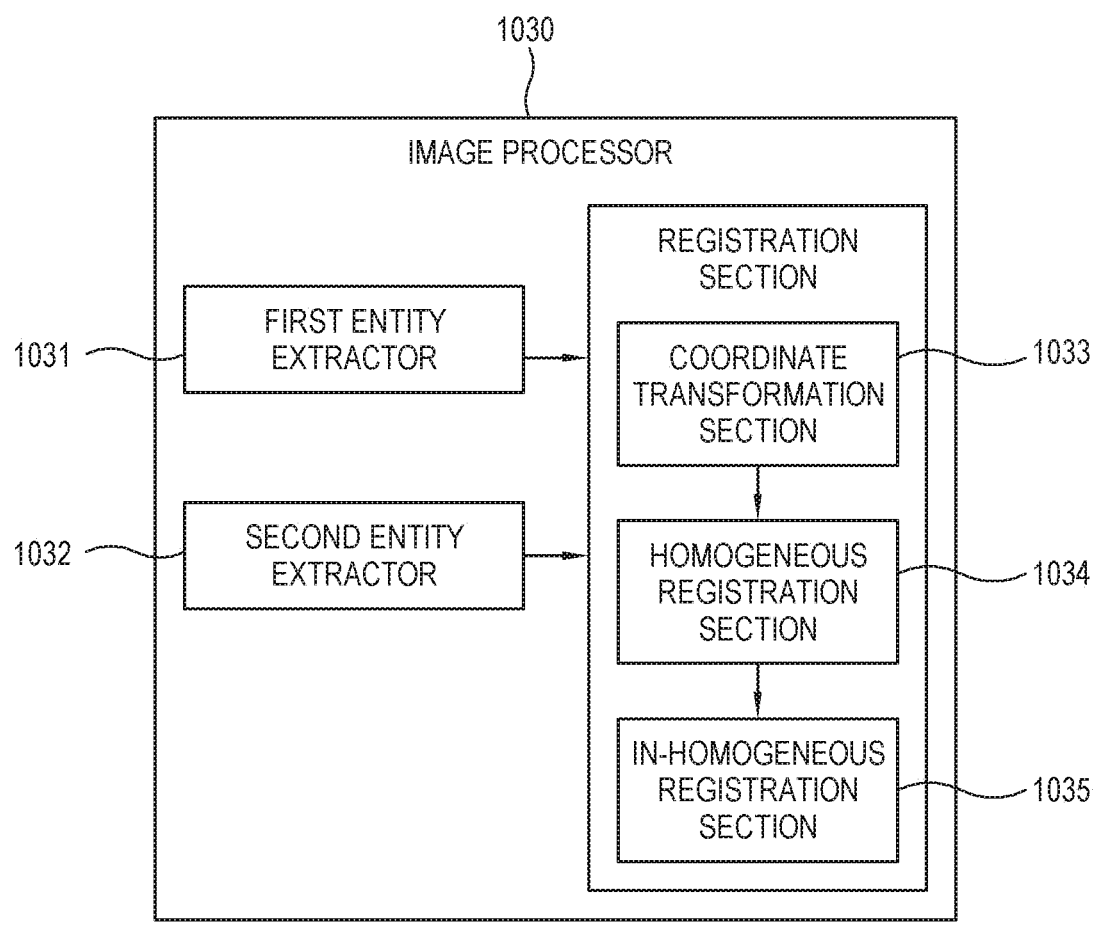
FIG. 11 is a block diagram for illustrating elements of the image processor of FIG. 10.

FIG. 10 is a block diagram for illustrating elements of a medical image display device 1000 according to one embodiment of the present disclosure, and FIG. 11 is a block diagram for illustrating elements of an image processor 1030 of FIG. 10, As shown in FIG. 10, the medical image display device 1000 according to one embodiment of the present disclosure includes a controller 1010, a display 1020, an image processor 1030, a user input section 1040, a storage 1050 and a communicator 1060. However, all the illustrated elements are not essential, and other general-purpose elements may be further provided in addition to the illustrated elements.

When the medical image display device 1000 is included in the MRI device 101 shown in FIG. 2, at least some elements of the medical image display device 1000 may be equivalent to those of the operator 260. Specifically, the image processor 1030 and the display 1020 may correspond to the image processor 262 and the output section 264 of FIG. 2, respectively. The controller 1010 may correspond to at least a part of the operator 260 and/or the display controller 248. Therefore, repetitive descriptions of the medical image display device 1000 with regard to those of FIG. 2 will be avoided.

Further, when the medical image display device 1000 is involved in the CT device 102 shown in FIG. 3 and FIG. 4, the controller 1010, the display 1020, the image processor 1030, the user input section 1040 and the storage 1050 may correspond to the controller 318, the display 330, the image processor 326, the user input section 328 and the storage 324 of FIG. 4, respectively. Therefore, repetitive descriptions of the medical image display device 1000 with regard to those of FIG. 3 or FIG. 4 will be avoided.

Further, the medical image display device 1000 may be involved in one of the server 534, the medical device 536 and the portable terminal 538 described with reference to FIG. 5 and the ultrasound device 610 described with reference to FIG. 6.

The display 1020 displays an application related to operations of the medical image display device. For example, the display 1020 may display a menu or a guide needed in diagnosis using the medical device. Further, the display 1020 may display an image obtained during the diagnosis, and a user interface (UI) for helping a user to control the medical image display device.

FIG. 10 shows an example that one display 1020 is provided in the medical image display device 1000, but the present disclosure is not limited thereto. Alternatively, the medical image display device 1000 may be configured to include a plurality of displays, for example, a main display and a sub display.

In this embodiment, the display 1020 displays a first image (or a first medical image) obtained by photographing an object including at least one anatomical entity, and/or a third image (or a third medical image) obtained by applying a registration process (to be described later) to the first image. Further, the display 1020 may further display a fourth image (or a fourth medical image) of showing an extended region of a lesion (to be described later). Further, the display 1020 may further display a second image (or a second medical image) as a reference image of the first image.

Here, the first image is the medical image obtained by photographing the object, which may include any medical image taken for diagnosis of diseases, such as an MRI image, a CT or the like tomography image, an X-ray image, an ultrasound image, etc.

The image processor 1030 processes the image to be displayed on the display 1020. Specifically, the image processor 1030 processes a signal obtained by taking an image of the object and makes it into an image to be displayable on the display 1020.

As an imaging method of the medical image, there is a method of taking an image of an object by emitting a beam such as an X-ray to the object like the X-ray imaging method. This imaging method is performed without separating an image-taking mode and a scanning mode. Further, this imaging method can directly take an image of an object without separately performing restoration or calculation for the image desired to be obtained.

There is another method of taking an image of an object by variously applying the image-taking mode or the scanning mode like an MRI or CT image. In this case, using various parameters that can be considered while scanning the object, it is possible to obtain images different in characteristic even though the images are obtained by photographing the same part of the body. That is, it is possible to obtain an image suitable for a purpose by changing the scanning mode in accordance with usage or purposes. Further, this imaging method can obtain a desired image by separately performing restoration or calculation for the image desired to be obtained.

Here, the technique used in taking a medical image by scanning an object is called a 'scan protocol' or a 'protocol'. Below, the 'protocol' will be used. Further, the image processor 1030 may generate a medical image by applying a predetermined protocol to obtained image data.

According to one embodiment of the present disclosure, a medical image display device 700 may generate calculated or post-processed image data (or the third image), using the image data (or the first image) obtained by applying the protocol. In this embodiment, the calculation or post-process includes a registration process, and the image subjected to the registration process becomes the third image and/or the fourth image.

The MRI device 101 obtains an MR signal by applying various protocols to scan an object, and uses the MR signal to generate an image of the object. Below, data obtained by scanning the object, for example, the MR signal or K-space data will be called the scan data, and the image of the object generated using the scan data will be called image data. The image data is equivalent to the foregoing first image.

The CT device 102 scans an object by applying different protocols in accordance with whether the contrast media is injected or not. Further, the image data obtained by the CT device 102 may become sinogram or projection data, and the image data, i.e. the first image may be generated using the obtained scan data.

The user input section 1040 is provided to receive a command from a user. The medical image display device 1040 in this embodiment receives an input for controlling the medical image display device 1040 from a user through the user input section 1040, and outputs the first medical image, the second medical image and/or the matched third medical image (or the fourth medical image) obtained by the medical image display device 1000 through the display 1020 in response to the received input.

The user input section 1040 may include a button, a keypad, a switch, a dial or a user interface displayed on the display 1020, i.e. a graphic user interface (GUI) for allowing a user to directly control the medical image display device 1040. According to an embodiment of the present disclosure, the user input section 1040 may include a touch screen provided on the display 1020.

In one embodiment, the medical image display device 1000 may receive section of at least one point on the medical image (or the first image) displayed on the display 1020 through the user input section 1040. Here, the selected point may correspond to the lymph node/blood vessel region in the non-contrast CT image (or the first image) of FIG. 9, and the image (or the third image) processed to distinguish between a lymph node and a blood vessel at the selected point by the registration process performed in the image processor 1030 is displayed in response to the selection of a user of the display 1020. The display 1020 may enlarge and display the selected point.

The storage 1050 stores data without limitations under control of the controller 1010. The storage 1050 may be materialized by a flash memory, a hard disc drive or the like nonvolatile storage medium. The storage 1050 is accessed by the controller 1010, and thus the controller 1010 is capable of reading/recording/modifying/deleting/updating the data.

The data stored in the storage 1050 may for example include not only an operating system for driving the medical image display device 1000, but also various applications executable in this operating system, image data, appended data, etc.

The storage 1050 in this embodiment may be configured to store various pieces of data related to the medical image. Specifically, the storage 1050 is configured to store at least one piece of image data generated by applying at least one protocol in the medical image display device 1000, and/or at least one piece of medical image data received from the outside. Further, the storage 1050 may be configured to additionally store at least one piece of image data generated by applying the registration process to the image data. The image data stored in the storage 1050 is displayed on the display 1050.

The communicator 1060 includes a wired/wireless network communication module for performing communication with various external devices. The communicator 1060 transmits a command/data/information/signal received from the outside to the controller 1010. Further, the communicator 1060 may transmit a command/data/information/signal received from the controller 1010 to the external device.

According to this embodiment, the communicator 150 is internally provided in the medical image display device 1000. However, according to one embodiment, the communicator may be materialized in the form of a dongle or a module and detachably connected to a connector (not shown) of the medical image display device 1000.

According to another embodiment, the communicator 1060 may include an input/output (I/O) port for connecting with human interface devices (HID). The medical image display device 1000 may use the I/O port to exchange the image data with a wired-connected external device.

The communicator 1060 in this embodiment may receive medical image data generated in another medical device. Here, another medical device may be the same kind of medical device as or different from the medical image display device 1000. For example, when the medical image display device 1000 is the CT device, another medical device may include another CT device. Optionally, another medical device may be the MRI device or the ultrasound device.

In one embodiment, the medical image display device 1000 may be directly connected to another medical device through the communicator 1060. According to another embodiment, the communicator 1060 may further include a connector for connecting with an external storage medium in which the medical image is stored.

The controller 1010 controls various elements of the medical image display device 1000. For example, the controller 1010 performs an imaging process/image registration process of the image processor 1030, and performs control corresponding to a command from the user input section 1040, thereby controlling general operations of the medical image display device 1000.

The controller 1010 includes at least one processor. At least one processor loads a program from a nonvolatile memory (e.g. ROM) storing the program to a volatile memory (e.g. RAM), and executes the program.

The controller 1010 according to this embodiment includes at least one general-purpose processor such as a central processing unit (CPU), an application processor (AP), and a microcomputer (MICOM), and loads and executes a program corresponding to a predetermined algorithm from the ROM to the RAM, thereby implementing various operations of the medical image display device 1000.

When the controller 1010 of the medical image display device 1000 is materialized by a single processor, e.g. a CPU, the CPU may be provided to implement various functions performable in the medical image display device 1000, such as various image processing processes for the medical image to be displayed on the display 1020, for example, selection of a protocol to be applied, imaging control corresponding to the selected protocol, following a command received through the user input section 1040, control of wired/wireless network communication with an external device, etc.

The processor may include a single-core processor, a dual-core processor, a triple-core processor, a quad-core processor, and the like multiple-core processor. The processor may include a plurality of processors, for example, a main processor and a sub processor. The sub processor is provided to operate in a standby mode (hereinafter, referred to as a sleep mode) in which it is supplied with only standby power and does not operate as the medical image display device 1000.

The processor, the ROM and the RAM included in the controller 1010 may be connected to one another by an internal bus.

According to one embodiment of the present disclosure, when the medical image display device 1000 is materialized by a laptop or desktop computer, the controller 1010 may further include a graphic processing unit (GPU, not shown) provided for a graphic process in a main body. Further, according to another embodiment, when the medical image display device 1000 is materialized by a portable terminal such as a smart phone, a smart pad, etc., the processor may include a GPU. For example, the processor may be materialized by a system on chip (SoC) where the core and the GPU are coupled.

Further, the controller 1010 may include a program for performing a specific function supported in the medical image display device 1000, for example, a function for sensing an error in a predetermined element including the main processor, and a chip provided as a dedicated processor for executing the program, for example, an integrated chip (IC).

In one embodiment, the controller 1010 may receive a user command for executing a predetermined application as a platform capable of analyzing the medical image through the user input section 1040. The executed application may include an input region 2220 (see FIG. 22) in which various buttons are displayed as an GUI for a user' selection, and a display region 2210 (see FIG. 22) in which the medical image is displayed.

A user can load an internally or externally stored medical image through the GUI of the input region of the application, and the loaded medical image is displayed on the display 1020 through the display region of the application. Further, a user may issue a command for registration between the first medical image and the second medical image in the executed application.

According to one embodiment of the present disclosure, the image processor 1030 may be materialized by a medical image analysis application, i.e. software to be driven by the controller 1010 including at least one processor as a hardware.

That is, the operations of the image processor 1030 to be described below are implemented by execution of software to be driven by the controller 1010. Therefore, it may be regarded that various operations performed in the image processor 1030 are implemented by the controller 1010, that is, at least one processor.

The controller 1010 of the medical image display device 1000 according to one embodiment of the present disclosure controls the image processor 1030 to apply the image registration process to the non-contrast medical image, i.e. the first medical image. Here, the image processor 1030 may use the first medical image and the second medical image to perform image registration with regard to the first medical image.

The second medical image is a contrast-enhanced medical image obtained at a different point of time, and is used as the reference image for the first medical image. For example, as an image obtained by photographing the object at a predetermined point of time in the past, the contrast-enhanced medical image may be stored in other medical devices, a server, etc. and loaded to the medical image display device 1000 through the communicator 1060, or may be previously stored in an internal or external storage 1050.

In one embodiment, the contrast-enhanced medical image may be a medical image obtained by photographing the same object as the first medical image, i.e. a medical image obtained by photographing the same patient in the past. A user may select the contrast-enhanced medical image usable as the second medical image based on history information about a patient. Here, a user may select at least one contrast-enhanced medical image as the second medical image. Further, the second medical image may be an image generated using the plurality of contrast-enhanced medical images obtained by photographing the same object in the past.

In another embodiment, the contrast-enhanced medical image may be a standardized medical image. For example, the standardized medical image may be generated using the contrast-enhanced medical images obtained by photographing objects having ages, sex, severity of diseases, and the like conditions similar to those of the object corresponding to the first medical image, based on information stored in a medical image database in which brain CT images of a plurality of objects are aggregated.

That is, an image registration using one contrast-enhanced medical image will be described below by way of example according to one embodiment. However, the plurality of contrast-enhanced medical images may be used in the image registration within the scope of the present disclosure.

The image processor 1030 segments the second medical image to extract at least one anatomical entity. Specifically, the image processor 1030 may extract reference region information corresponding to at least one anatomical entity from a second medical image, i.e. the reference image of the first medical image.

Here, there may be a plurality of anatomical entities, and thus the image processor 1030 may further extract from the second medical image a region corresponding to the first entity (hereinafter, referred to as the first anatomical entity) and a region corresponding to a second entity (hereinafter, referred to as the second anatomical entity) different from the first entity.

In one embodiment, the first entity may be a blood vessel, and the second entity may be a lymph node. Further, in another embodiment, the first entity may be a blood vessel, and the second entity may be a bronchial tube.

The image processor 1030 uses the reference region information extracted from the second medical image for registration between the first medical image and the second medical image. Here, the image subjected to the registration is displayed as the third medical image on the display 1020. The region of detected anatomical entity is displayed to be distinguished from at least one region unrelated to detected anatomical entity in the third medical image.

Here, the image processor 1030 may use a geometric relationship between the anatomical entity of the first medical image and the anatomical entity of the second medical image in performing the image registration, in which the geometric relationship may include a vector of showing a relative position between the anatomical entities.

The registration for the medical images includes a process of matching coordinates of the first medical image and the second medical image with each other. In this embodiment, each of the first medical image and the second medical image may be a medical image generated using a coordinate system based on the DICOM.

The image processor 1030 calculates a coordinate transformation function for transformation of the coordinates of the second medical image into the coordinates of the first medical image or inverse transformation, through the registration of the first medical image and the second medical image. Here, the coordinate transformation function may include a first transformation in which a previous unique characteristic of the anatomical entity calculated during the homogeneous registration process (to be described later) is maintained, and a second transformation in which two pieces of image information calculated during the in-homogeneous registration are exactly matched with each other.

The image processor 1030 may use the coordinate transformation function to synchronize the coordinates and views of the first medical image and the second medical image.

In one embodiment, the registered image may be an image transformed from the first medical image. In another embodiment, the registered image may be a fusion image where the first medical image and the second medical image are fused. The display 1020 displays a first medical image, and displays the third medical image and/or the fourth medical image generated by the registration between the first medical image and the second medical image.

Figure 12:
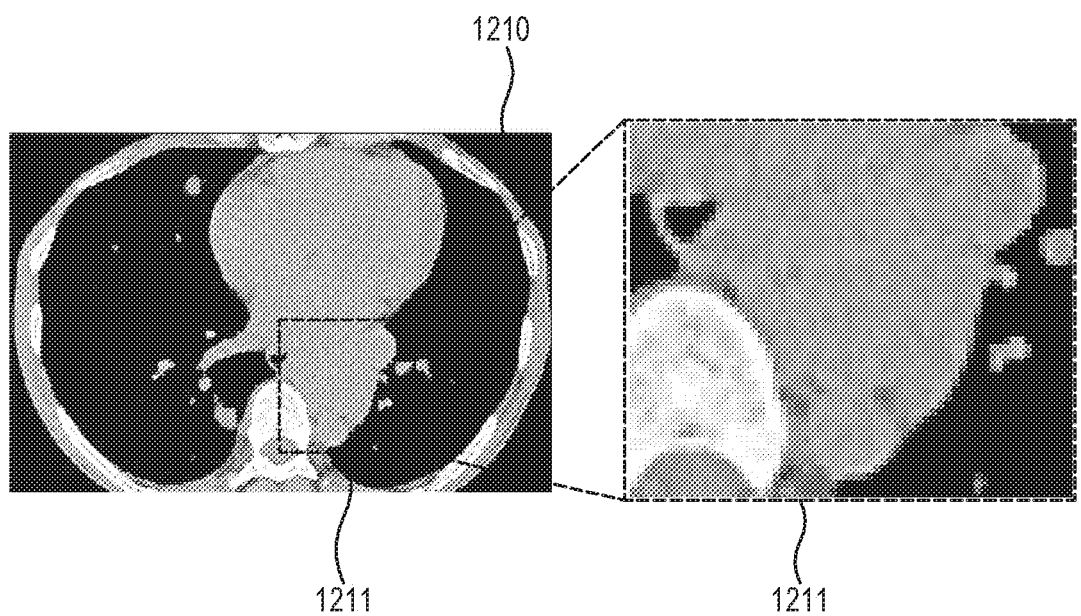
FIG. 12 is a view for illustrating a first medical image according to one embodiment of the present disclosure.

FIG. 12 is a view for illustrating a first medical image 1210 according to one embodiment of the present disclosure.

In this embodiment, the first medical image 1210 is a relatively recent image obtained by photographing the object. The first medical image 1210 is a non-contrast image obtained in the state that a contrast medium is not injected to the object, and may for example be a brain CT image as shown in FIG. 12. Alternatively, the first medical image 1210 may be an image that can be displayed in real time, for example, an ultrasound image.

As shown in FIG. 12, the first medical image 1210 is the non-contrast CT image, and it is thus not easy to distinguish, i.e. identify between the first entity and the second entity, that is, the blood vessel and the lymph node within the image 1210, A user may use the user input section 1040 to select a region 1211, in which the blood vessel and the lymph node are expected to be located, in the first medical image 1210. The controller 1010 may control the display 1020 to enlarge and display the selected region 1211 as shown in FIG. 12. Even in the enlarged region 1211, the blood vessel and the lymph node are not distinguishable.

Figure 13:
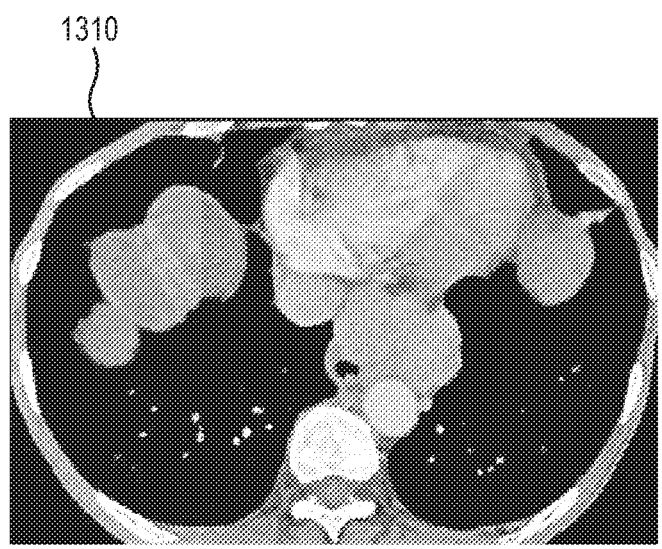
FIG. 13 is a view for illustrating a second medical image according to one embodiment of the present disclosure.
Figure 14:
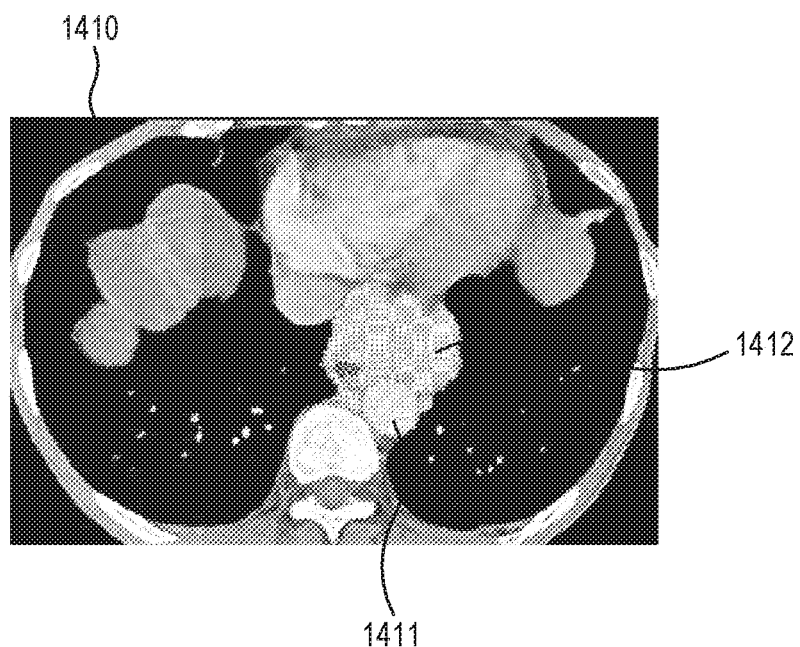
FIG. 14 is a view for illustrating the second medical image in which an entity is extracted.

FIG. 13 is a view for illustrating a second medical image 1310 according to one embodiment of the present disclosure, and FIG. 14 is a view for illustrating the second medical image 1410 in which an entity is extracted.

The second medical image 1310 is a contrast-enhanced image obtained in the state that a contrast medium is injected into an object, and may for example be a brain CT image as shown in FIG. 13 and FIG. 14.

Referring to FIG. 11, the image processor 1030 includes a first entity extractor 1031, a second entity extractor 1032, and a registration part. The registration part includes a coordinate transformation section 1033, a homogeneous registration section 1034, and an in-homogeneous registration section 1035.

In one embodiment, it is illustrated that the image processor 1030 includes the first entity extractor 1031 and the second entity extractor 1032 to extract two anatomical entities, but not limited thereto. That is, more anatomical entities, for example, three or more anatomical entities may be extracted, and distinguishable through the third medical image.

Further, in another embodiment, the image processor 1030 may include one entity extractor to extract a region of a first entity from the second medical image, and displays the region of the first entity to be distinguishable from at least one region of at least one entity other than the first entity. For example, the first entity region may be a blood-vessel region, and the blood-vessel region and the non-blood-vessel region are displayed to be distinguishable between them. Here, the non-blood-vessel region includes a lymph-node region. In another embodiment, the non-blood-vessel region may include a bronchial-tube region.

The first entity extractor 1031 and the second entity extractor 1032 respectively extract region information of the first anatomical entity and region information of the second anatomical entity from the second medical image. The extracted regions of the first entity and the second entity are reference regions, and the extracted region information is utilized by the registration section as reference region information.

The first entity extractor 1031 extracts the region corresponding to the first entity from the second medical image based on an anatomical characteristic of the first entity, and the second entity extractor 1032 extracts the region corresponding to the second entity from the second medical image based on an anatomical characteristic of the second entity.

The first entity extractor 1031 may employ a brightness level of each pixel included in the second medical image to determine the region of the first entity.

Specifically, the first entity extractor 1031 detects points having brightness levels within a first preset range in the contrast-enhanced second medical image, and determines the region corresponding to the first entity concerned with the detected points. Alternatively, when specific points are selected within the second medical image through the user input section 1040, the first entity extractor 1031 detects points, of which difference in brightness level from the selected points, i.e. contrast is lower than or equal to a first threshold, in order to detect points having anatomical characteristics similar to those of the selected points, thereby determining the first entity region concerned with the detected points.

The second entity extractor 1032 detects points having brightness levels within a second preset range in the contrast-enhanced second medical image, and determines the region corresponding to the second entity concerned with the detected points. Alternatively, when specific points are selected within the second medical image through the user input section 1040, the second entity extractor 1032 detects points, of which difference in brightness level from the selected points, i.e. contrast is lower than or equal to a second threshold, in order to detect points having anatomical characteristics similar to those of the selected points, thereby determining the second entity region concerned with the detected points.

The first range and the second range for the brightness level may be previously set corresponding to the respective anatomical characteristics of the first entity and the second entity. Likewise, the first threshold and the second threshold may be previously set corresponding to the respective anatomical characteristics of the first entity and the second entity. As necessary, the first threshold and the second threshold may be set to have the same value.

The controller 1010 may control the display 1020 to display the first entity region 1411 and the second entity region 1412, i.e. the reference regions extracted from the second medical image to be distinguishable from each other as shown in FIG. 14. Through the displayed image 1410 of FIG. 14, a user checks the blood vessel region 1411 corresponding to the first entity and the lymph node region 1412 corresponding to the second entity, and uses them in diagnosis.

Information about the first entity region and information about the second entity region respectively extracted by the first entity extractor 1031 and the second entity extractor 1032 are transmitted to the registration section.

The registration section makes registration between the first medical image and the second medical image based on a predetermined algorithm. The registration section uses the reference region information, i.e. the information about the first entity region received from the first entity extractor 1031 and the information about the second entity region received from the second entity extractor 1032, thereby achieving the registration between the first medical image and the second medical image.

That is, the first entity region 1411 and the second entity region 1412 divided from the second medical image are matched to the first entity region and the second entity region of the first medical image through the image registration process of the registration section in the image processor 1030.

Figure 15:
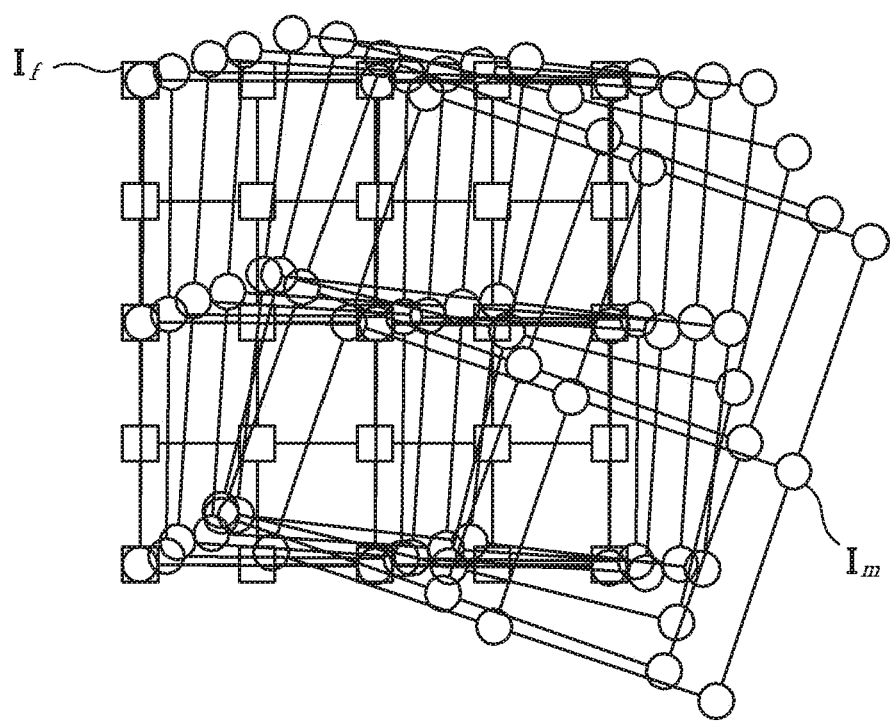
FIG. 15 is a view for describing an image registration process according to the present embodiment.

FIG. 15 is a view for describing an image registration process according to the present embodiment.

In the medical image display device 1000 according to the embodiment of the present disclosure, as shown in FIG. 15, the image registration includes a process of transforming different sets of image data, i.e. $I_f$ and $I_m$, in a captured same scene into one coordinate system, and is achieved by optimization algorithms for maximizing similarity between the images $I_f$ and $I_m$ to be subjected to the registration and minimizing costs.

For example, the image registration include a process of finding a final parameter $P_{final}$, which maximizes a result value of a similarity measurement function as shown in the following expression 1 or minimizes a result value of a cost function as shown in the following expression 2, based on a predetermined transformation model parameter. Here, the process of finding the final parameter may include the homogeneous registration and the in-homogeneous registration to be described later.

$$p_{final} = \underset{p}{\operatorname{argmax}} S(I_f, I_m : p) \qquad \text{[Expression 1]}$$

$$p_{final} = \underset{p}{\operatorname{argmax}} C(I_f, I_m : p) \qquad \text{[Expression 2]}$$

Here, $I_f$ is a fixed image, e.g. the first medical image of the non-contrast image, and $I_m$ is a moving image, e.g. the second medical image of the contrast-enhanced image. Further, S is the similarity measurement function, C is the cost function, and P is a parameter set of a transformation model.

The transformation model parameter usable in the foregoing embodiments of the present disclosure includes rigid transformation, affine transformation, thin-plate-spline free form deformation (TPS FFD), B-spline FFD, an elastic model, etc.

Further, a result value of the cost function may be determined by weights respectively given to a similarity or dis-similarity measurement function and regularization metric.

The similarity or dis-similarity measurement function includes mutual information (MI), normalized mutual information (NMI), gradient-magnitude, gradient-orientation, sum of squared difference (SSD), normalized gradient-vector flow (NGF), gradient NMI (GNMI), etc. Further, the regularization metric includes volume regularization, diffusion regularization, curvature regularization, local rigidity constraint, etc.

The coordinate transformation section 1033 maps coordinate systems of the first medical image and the second medical image to each other. Here, the coordinate system mapping refers to matching the coordinate system of the first medical image with the coordinate system of the second medical image. For example, the coordinate transformation section 1033 may align the coordinate system of the second medical image so that the first anatomical entity (i.e. the reference region) of the second medical image can be arranged along the arranged orientation of the first anatomical entity of the first medical image. Here, the coordinate transformation section 1033 may rotate or move the second medical image as long as the first anatomical entities of the first medical image and the second medical image are not misaligned.

According to one embodiment of the present disclosure, the image processor 1030 sequentially performs the homogeneous registration and the in-homogeneous registration with regard to the first medical image and the second medical image, of which the coordinate systems are aligned through the coordinate transformation section 1033.

Figure 17:
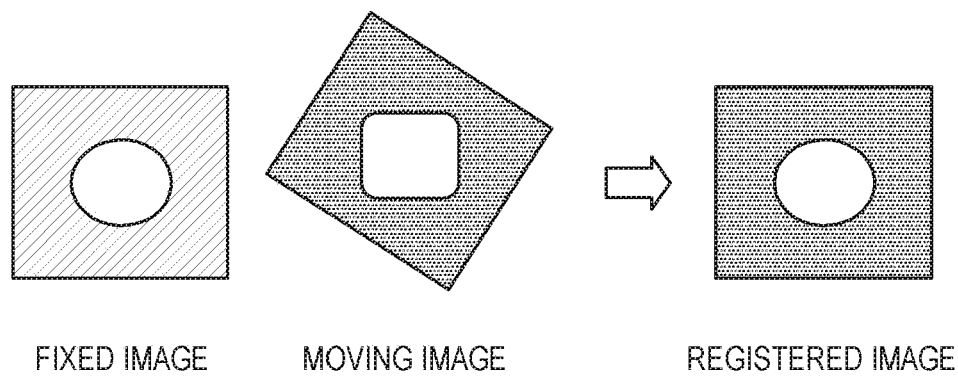
FIG. 17 is a view for conceptually illustrating an in-homogeneous registration process.

FIG. 16 is a view for conceptually illustrating a homogeneous matching process, and FIG. 17 is a view for conceptually illustrating an in-homogeneous matching process.

As shown in FIG. 16, the homogeneous registration refers to that an image characteristic (shape) of a moving image is maintained and matched with a fixed image at the image registration.

As shown in FIG. 17, the in-homogeneous registration refers to that the image characteristic (shape) of the moving image is transformed and exactly matched with a fixed image at the image registration.

In one embodiment, the homogeneous registration section 1034 and the in-homogeneous registration section 1035 compute the cost function through the transformation process between the coordinate matched images $I_f$ and $I_m$ to be subjected to the registration, and repetitively performs the process of updating the parameter P based on the computed cost function, thereby obtaining a final parameter $P_{final}$ of minimizing the result value of the cost function.

Here, the homogeneous registration is performed in such a manner that the weights given to the similarity (or dis-similarity) measurement function and the regularization metric are gradually changed, and then the in-homogeneous registration is performed, in which the change of the weights may be achieved to increase a degree of freedom of the second medical image used as the moving image.

That is, for convenience, FIG. 11 illustrates that the image processor 1030 includes the homogeneous registration section 1033 and the in-homogeneous registration section 1034, but the homogeneous registration and the in-homogeneous registration are not completely separable processes, in which some former-half processes in the processes of changing the weights to update P correspond to the homogeneous registration, and the other latter-half processes correspond to the in-homogeneous registration.

Further, FIG. 11 illustrates that the processes are repetitively performed until the in-homogeneous registration is completed after the homogeneous registration is completed. However, the present disclosure may be implemented to perform only the homogeneous registration without performing the in-homogeneous registration.

Figure 18:
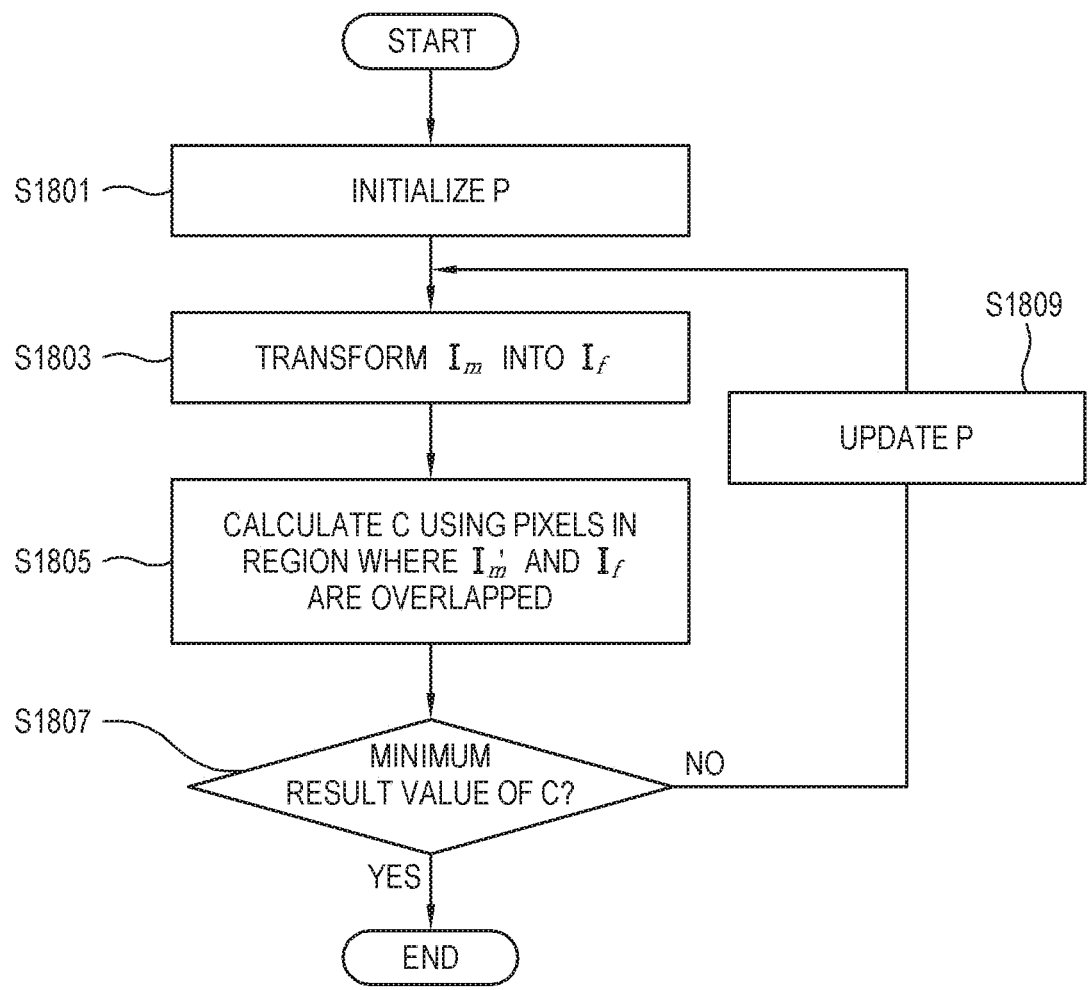
FIG. 18 is a flowchart of illustrating a procedure for performing a registration process according to one embodiment of the present disclosure.

FIG. 18 is a flowchart of illustrating a procedure for performing the registration process according to one embodiment of the present disclosure, In one embodiment, the image processor 1030 may induce other results from the homogeneous registration and the in-homogeneous registration in such a manner of designing the regularization metric for the transformation model and the cost function, through the process of continuously updating P in the algorithm of FIG. 18. In this process, a rigid global model, a non-rigid global model, a rigid local model, a non-rigid local model, or the like known model is used.

Referring to FIG. 18, the image processor 1030 first initializes the transformation model parameter P (S1801).

Then, the second medical image is transformed so that the second medical image $I_m$ can be aligned with the coordinate system of the first medical image $I_f$ (S1803). In one embodiment, the coordinate system of the affine space may be used in the mapping of the coordinate system, and the process S1803 in this case S1803 is also called affine registration.

Next, the cost function C is calculated using pixels in regions where the second medical image $I_{m'}$ transformed in the process S1803 and the first medical image $I_f$ are overlapped (S1805). Here, the result value of the cost function C is determined using the similarity (or dis-similarity) measurement function and the regularization metric based on prior information, and may be for example determined by the sum of weights given to the similarity measurement function and the regularization metric. For example, the overlapped regions may be regions corresponding to at least one anatomical entity.

The image processor 1030 determines whether the cost function C calculated in the process of S1805 has the minimum result value (S1807).

In accordance with the determination results in the process S1807, the transformation model parameter P is updated (S1809).

The image processor 1030 repetitively performs the processes from S1803 to S1807 until the cost function obtains the minimum result value, based on the determination result from the process of S1807. This process is the processes of the homogeneous registration and the in-homogeneous registration to find optimization algorithms with regard to each process.

Through the foregoing processes, the homogeneous registration section 1034 obtains first transformation formula information as the optimization algorithm in which unique characteristics of the previous lymph node and blood vessel information are maintained.

Further, the in-homogeneous registration section 1035 obtains second transformation formula information as the optimization algorithm in which two pieces of image information are exactly matched. In one embodiment, the in-homogeneous registration may be a quantifying process for tracing change in the second anatomical entity, for example, the lymph node. By this quantification, a change degree in the lymph node may be digitized to be displayed in the medical image.

Here, through the similarity (or dis-similarity) measurement function, image matching between $I_f$ and $I_m$ may be evaluated, and the weights given to the similarity (or dis-similarity) measurement function and the regularization metric may be factors for distinguishing between the homogeneous registration and the in-homogeneous registration.

In one embodiment, the image processor 1030 generates a third medical image from the first medical image in accordance with the foregoing homogeneous registration process. Further, a fourth medical image may be further generated from the third medical image in accordance with the in-homogeneous registration process.

The controller 1010 controls the display 1020 to display the third medical image and/or the fourth medical image generated by the image processor 1030.

Figure 19:
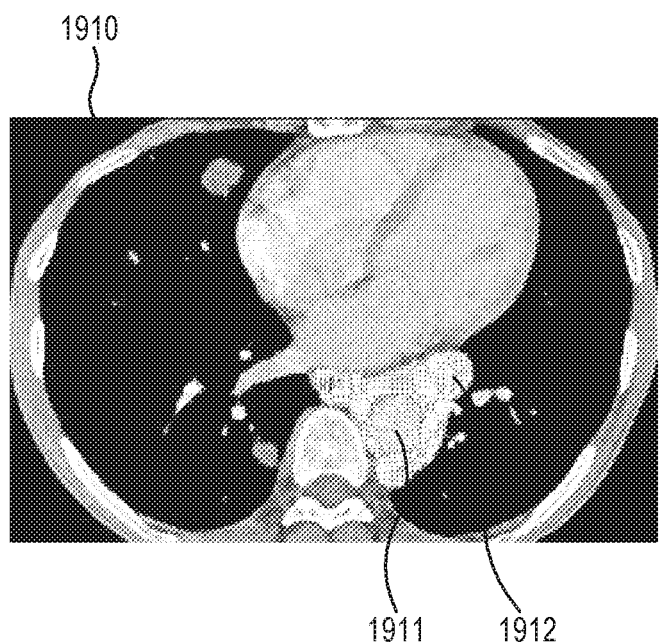
FIG. 19 is a view for illustrating a third medical image according to one embodiment of the present disclosure.
Figure 20:
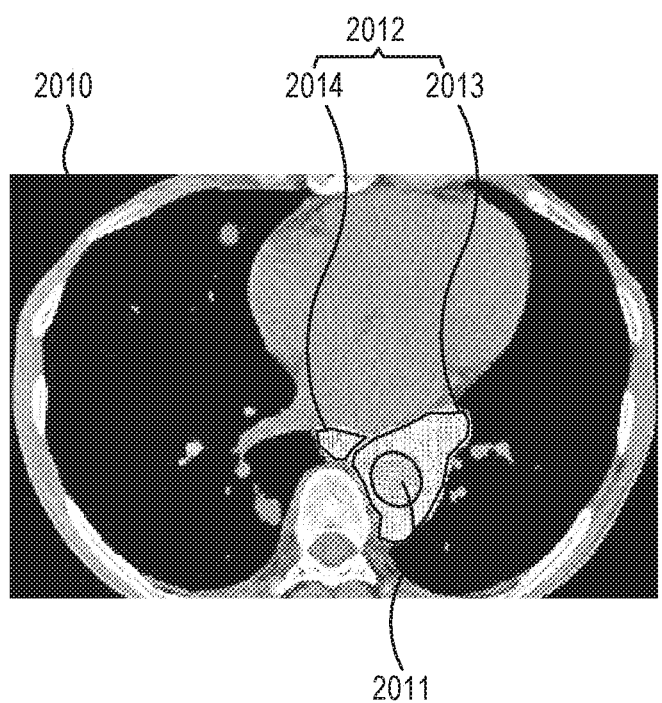
FIG. 20 is a view for illustrating a fourth medical image.
Figure 21:
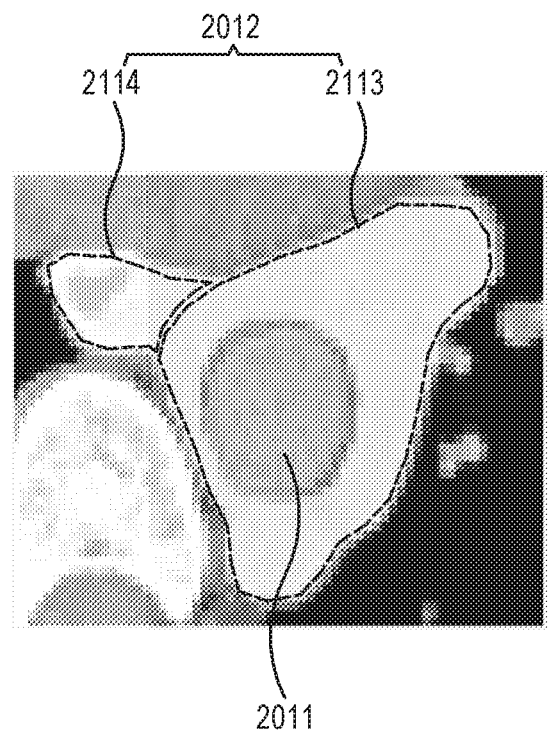
FIG. 21 is an enlarged view for illustrating some entity regions of FIG. 20.

FIG. 19 is a view for illustrating a third medical image 1910 according to one embodiment of the present disclosure, FIG. 20 is a view for illustrating a fourth medical image 1610, and FIG. 21 is an enlarged view for illustrating some entity regions of FIG. 20.

As shown in FIG. 19, the controller 1010 may control the display 1020 to display a first entity region 1911 and a second entity region 1912 to be distinguishable in the third medical image generated by the homogeneous registration. Therefore, a user may check the blood vessel region 1911 corresponding to the first entity and the lymph node region 1912 corresponding to the second entity, which are not distinguishable in FIG. 12, and use them in diagnosis.

Here, the controller 1010 may control the display 1020 to display the region of the detected anatomical entity to be distinguishable from the regions of non-anatomical entity, by at least one among a color, a pattern, a pointer, a highlight and an animation effect. If a plurality of regions is present corresponding to the detected anatomical entity, the color, the pattern, the pointer, the highlight and the animation effect may be differently applied to the plurality of regions. Further, the color, pattern, pointer, highlight and animation effects may be combined and applied to the plurality of regions. For example, the first entity region 1911 may be displayed to be distinguishable with the colors, and the second entity region 1912 may be displayed distinguishable with the patterns. Alternatively, a predetermined pattern and pointer may be given to the first entity region 1911 to be distinguishable from other regions, and the like various alternatives are possible.

That is, FIG. 19 illustrates that the detected first entity region 1911 and second entity region 1912 are displayed to be distinguishable with the patterns, by way of example. Besides, various embodiments for allowing a user to visually distinguish between them are possible.

Here, the pattern may include a plurality of horizontal lines, vertical lines, oblique lines in a predetermined direction, dot patterns having various shapes such as a circle, wave patterns, etc. The pointer may include a solid line and various dotted lines to be marked along the circumference of the detected region, and may be brighter than surrounding regions. The highlight may include making the detected region different in brightness from other regions, for example, brighter than other regions. The animation effect may include applying various visual effects such as flickering at intervals of predetermined time, gradual brightening/dimming, and the like to the detected region.

As shown in FIG. 19, the distinguishable display for the regions 1911 and 1912 of the anatomical entities may be activated or inactivated by a user's selection. That is, a user may control the user input section 1040 to activate the function of displaying the first region 1911 and the second region 1912 to be distinguishable with colors or the like, and a user may make an input for activating the function.

To this end, a user interface, i.e. GUI for selecting whether to activate the distinguishability of the entity may be displayed on the display 1020, or the user input section 1040 may include a toggle switch assigned corresponding to the entity distinguishing function. In such various ways, a user can make the selection.

Further, a level (i.e. a degree, a grade, etc.) of displaying the distinguishability of the detected anatomical entity may be adjusted through the user input section 1040. That is, the medical image display device 1000 according to the present disclosure may display the distinguishability of the anatomical entities in various ways in accordance with a user's preference, taste, etc.

By the way, as shown in FIG. 20, a fourth medical image 2010 subjected to the in-homogeneous registration not only shows the first entity region 2011 and the second entity region 2012 to be distinguishable, but also shows even a traced change in the second entity region 2012 of a previous point of time. Here, the previous point of time may refer to a point of time when the second medical image is obtained.

Thus, a lesion expansion region 2014 is displayed in a lymph node region 2012, thereby facilitating a user's diagnosis.

A user may issue a command of enlarging and displaying a predetermined region through the user input section 1040, and thus, as shown in FIG. 21, a blood vessel region 2111 corresponding to the first entity and a lymph node region 2112 corresponding to the second entity are distinguishably displayed in a fourth medical image 2110, and a previous lesion region 2113 and a lesion expansion region 2114 are distinguishably in the lymph node region 2112, so that a user can determine a degree of expanded lesion and use it in diagnosis.

The controller 1010 may control the display 1020 to display the previous lesion regions 2013 and 2113 and the lesion expansion regions 2014 and 2114 to be distinguishable in FIG. 20 and FIG. 21, by at least one of the color, the pattern, the pointer, the highlight and the animation effect. Here, the controller 1010 may combine and apply the color, the pattern, the pointer, the highlight and the animation effect to the previous lesion regions 2013 and 2113 and the lesion expansion regions 2014 and 2114. For example, the previous lesion regions 2013 and 2113 may be distinguishable by the pattern, and the lesion expansion regions 2014 and 2114 may be distinguishable by the pointer. In addition, a predetermined pattern and highlight may be given to the lesion expansion regions 2014 and 2114 to be distinguishable from other regions. Besides, various alternatives are possible.

As shown in FIG. 20 and FIG. 21, the distinguishable display for the lesion expansion regions 2014 and 2114 may be activated or inactivated by a user's selection. That is, a user may control the user input section 1040 to activate the function of displaying the lesion expansion regions 2014 and 2114 to be distinguishable with the color or the like, and a user may makes a user input for activating the function.

To this end, a user interface, i.e. GUI for selecting whether to activate the distinguishability of the region may be displayed on the display 1020, or the user input section 1040 may include a toggle switch assigned corresponding to the region distinguishing function. In such various ways, a user can make the selection. A user makes selection to activate/inactivate the distinguishability of the expansion region, and thus easily determine an expansion degree of lesion.

Further, a level (i.e. a degree, a grade, etc.) of displaying each distinguishability of the previously detected lesion regions 2013 and 2113 and the lesion expansion regions 2013, 2114 may be adjusted through the user input section 1040. That is, the medical image display device 1000 according to the present disclosure may display the distinguishability of the anatomical entities in various ways in accordance with a user's preference, taste, etc.

Figure 22:
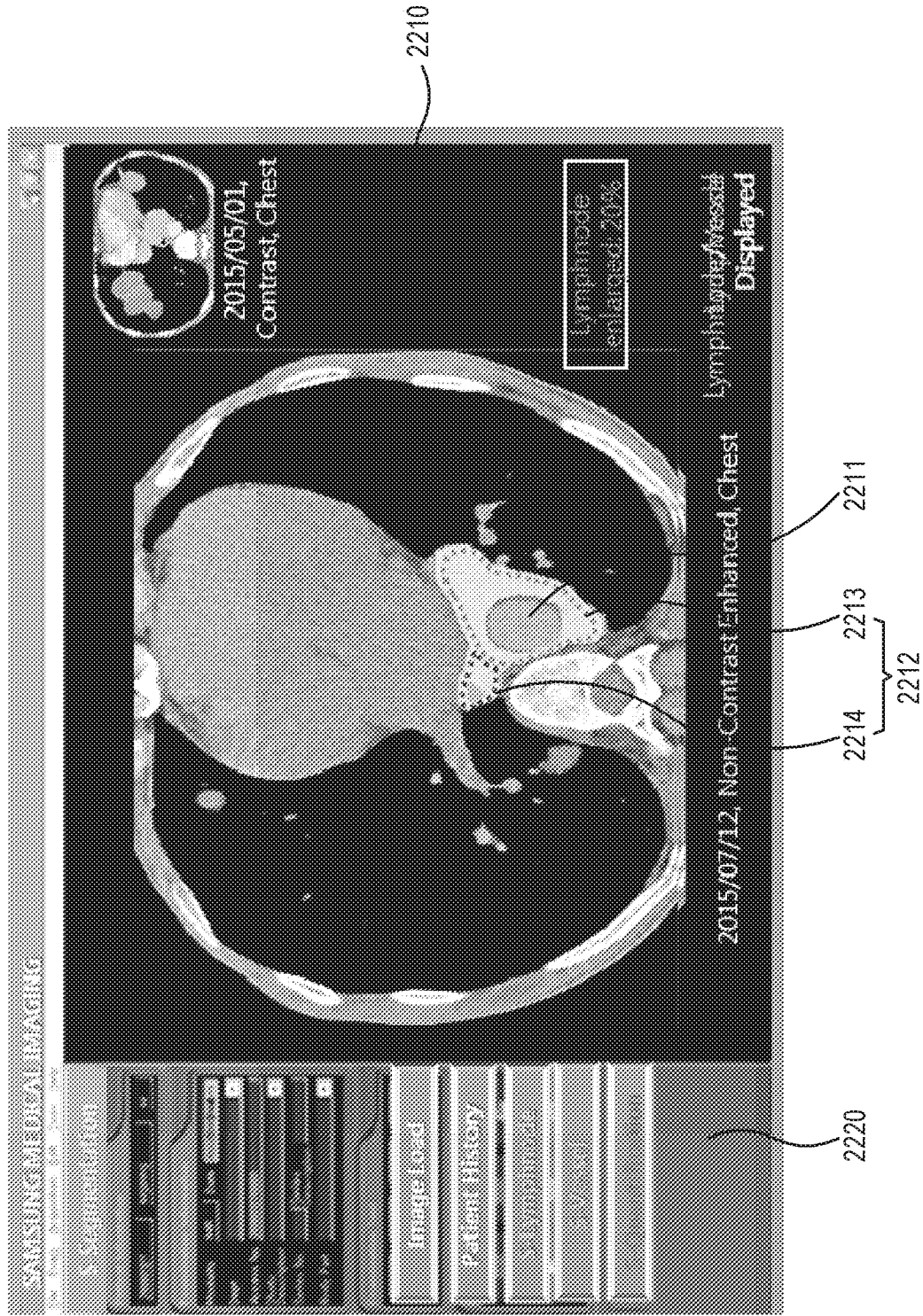
FIG. 22 is a view for illustrating a screen displayed by driving an application having a medical diagnosis function in the medical image display device according to one embodiment of the present disclosure.

FIG. 22 is a view for illustrating a screen displayed by driving an application having a medical diagnosis function in the medical image display device according to one embodiment of the present disclosure.

A medial image 2210 shown in FIG. 22 is an image of showing a result from an image registration process, in which a user interface, i.e. an input region 2220 including various GUIs is placed at a left side of a display region where a first anatomical entity 2211, a second anatomical entity 2112, and a previous lesion region 2113 and a lesion expansion region 2114 within the second anatomical entity 2112 are displayed to be distinguishable from one another.

In the state that a first medical image is displayed on the display region 2110 in an executed application, a user selects a predetermined button on the user interface of the input region 2220 to load a reference image used as a second medical image, thereby utilizing the loaded reference image in image registration for the first medical image.

That is, the display region 2210 of FIG. 22 may display various medical images including the images shown in FIG. 12 to FIG. 14 and FIG. 19 to FIG. 21. Further, by dividing the region with regard to the display region 2210, two or more images including the images of FIG. 12 to FIG. 14 and FIG. 19 to FIG. 21 are displayed in a horizontal and/or vertical direction to be compared with one another.

In addition, when the display 1020 includes a plurality of displays, for example, a main display and a sub display, two or images may be distinguishably displayed by various combinations.

FIG. 23 to FIG. 26 are views for illustrating various examples of utilizing image matching for a diagnosis in the medical image display device 1000 according to one embodiment of the present disclosure.

Figure 23:
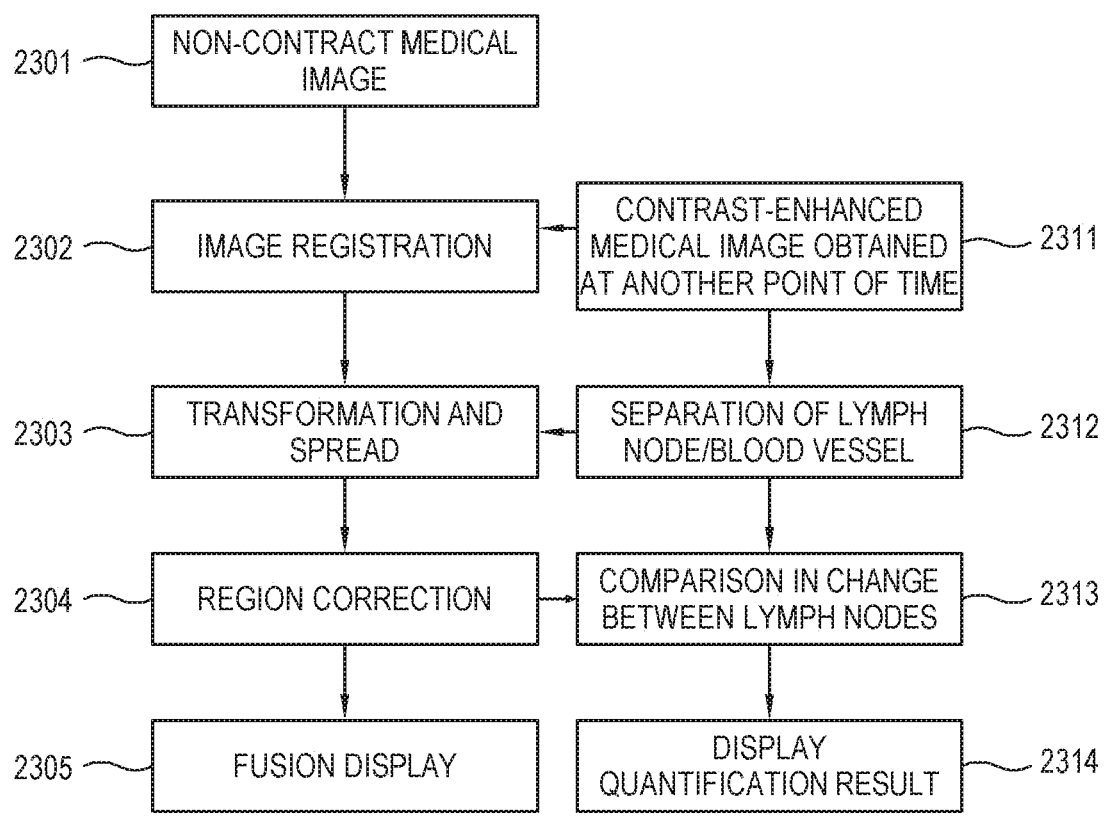
FIG. 23 to FIG. 26 are views for illustrating various examples of utilizing image registration for a diagnosis in the medical image display device according to one embodiment of the present disclosure.

In one embodiment of the present disclosure shown in FIG. 23, as described above, the controller 1010 of the medical image display device 100 obtains a first medical image (i.e. a non-contrast medical image) (2301) and a second medical image (i.e. a contrast enhanced medical image obtained at another point of time) (2311), and generates a fusion display based on their registration.

A process of generating the fusion display may include image registration (2302) between the non-contrast medical image and the contrast enhanced medical image obtained at another point of time, transformation and spread (2303) of the image generated by the registration, and region correction (2304).

Here, the contrast-enhanced medical image obtained at another point of time is divided into predetermined anatomical entities, that is, lymph node and blood vessel regions (2312), and subjected to the transformation and spread (2303) for matching coordinates of these two medical images and the region correction (2304). When the region correction (2304) is completed, a fused image is displayed as a registration image (2305).

As the image is sequentially subjected to the registration, the transformation and the spread, and the correction, comparison in change of the lymph node between the contrast-enhanced medical image obtained at another point of time and the non-contrast medical image obtained at this time is quantified (2313), and a result of quantification is displayed.

Figure 24:
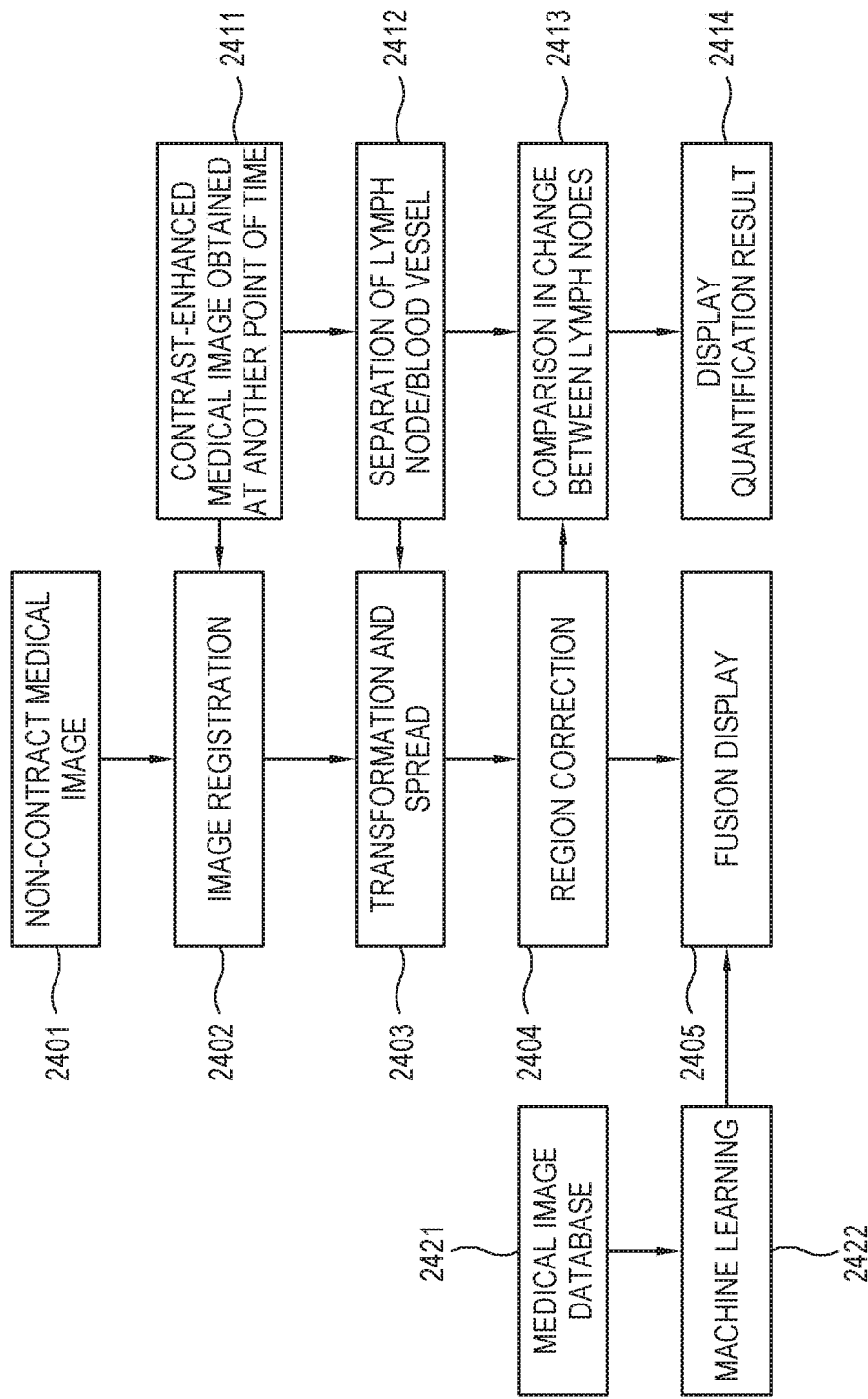

In another embodiment shown in FIG. 24, the controller 1010 of the medical image display device 100 obtains a first medical image (i.e. a non-contrast medical image) (2401) and a second medical image (i.e. a contrast enhanced medical image obtained at another point of time) (2411), and generates a fusion display based on their registration. In this process, data is loaded from a medical image database (2421), and machine learning is performed (2422). These may be further utilized in the region correction (2404).

The medical image database stores various pieces of information, and the controller 1010 assorts data (including images) having conditions (age, sex, severity of lesion, etc. of an object) similar to the object among the pieces of stored information, and performs machine learning for predicting data through a training process using the assorted data.

The controller 1010 may control the image processor 1030 to utilize the data predicted by the machine learning in separation and quantification in the image registration process of another embodiment. This case may be improved in accuracy of the image registration, as compared with the embodiment of using only the reference information extracted from the second image (i.e. the contrast-enhanced medical image obtained at another point of time.

A process of generating the fusion display may include image registration (2401) between the non-contrast medical image and the contrast enhanced medical image obtained at another point of time, transformation and spread (2402) of the image generated by the registration, and region correction (2403).

Here, the contrast-enhanced medical image obtained at another point of time is divided into predetermined anatomical entities, that is, lymph node and blood vessel regions (2412), and subjected to the transformation and spread (2403) for matching coordinates of these two medical images and the region correction (2404). When the region correction (2404) is completed, a fused image is displayed as a registration image (2405).

As the image is sequentially subjected to the registration, the transformation and the spread, and the correction, comparison in change of the lymph node between the contrast-enhanced medical image obtained at another point of time and the non-contrast medical image obtained at this time is quantified (2413), and the data based on the machine learning is further utilized in the quantification. Then, a result of quantification is displayed (2414).

Figure 25:
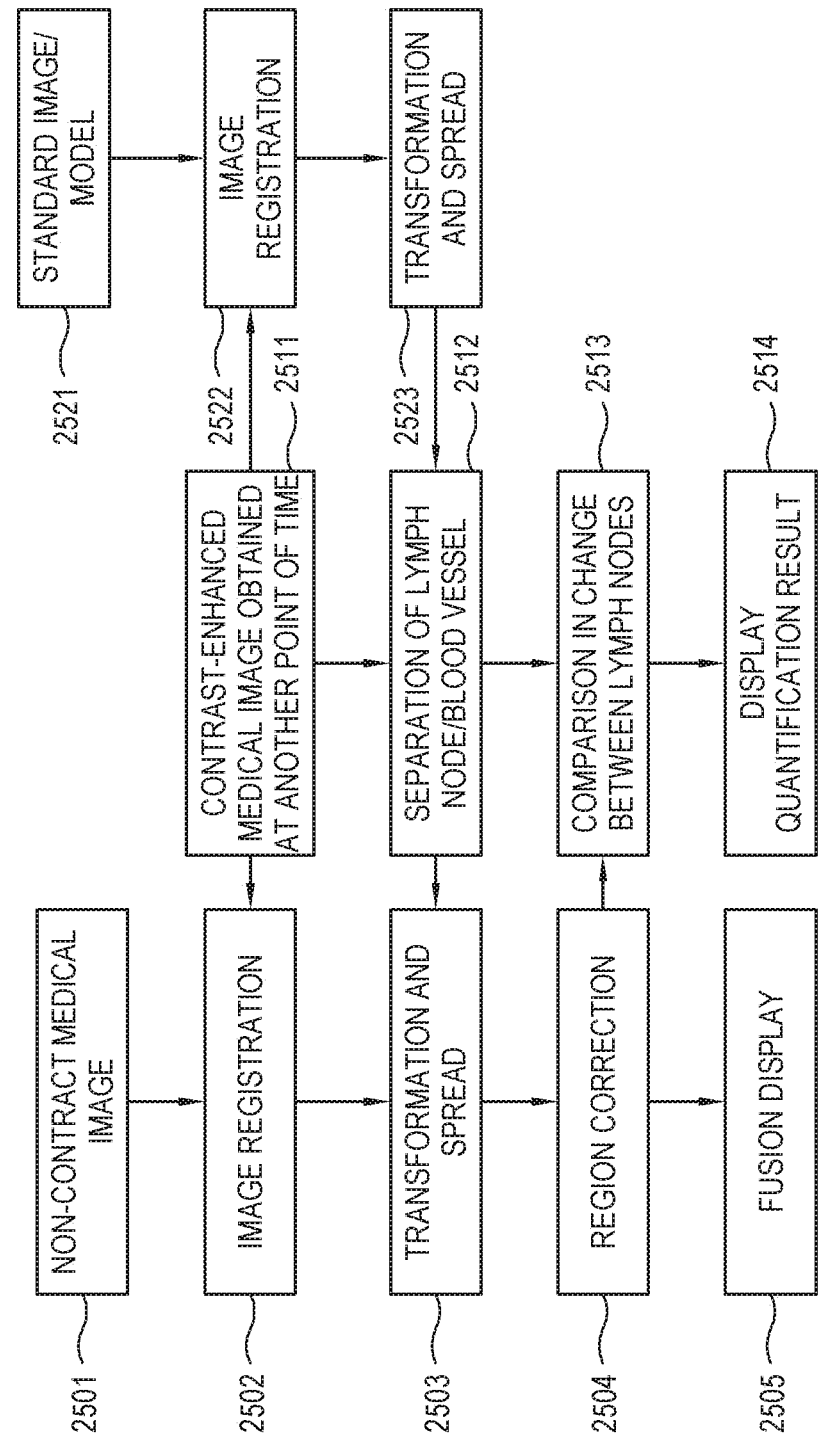

In still another embodiment shown in FIG. 25, the controller 1010 of the medical image display device 100 obtains a first medical image (i.e. a non-contrast medical image) (2501) and a second medical image (i.e. a contrast enhanced medical image obtained at another point of time) (2511), and generates a fusion display based on their registration. In this process, a standard image/model may be further utilized. For example, the controller 1010 loads a plurality of images corresponding to conditions (age, sex, severity of lesion, etc. of an object) similar to the object from data stored in the standard image/model (2501), and applies the image registration (2522) and the transformation and spread (2523) to the loaded images.

A process of generating the fusion display may include image registration (2502) between the non-contrast medical image and the contrast enhanced medical image obtained at another point of time, transformation and spread (2503) of the image generated by the registration, and region correction (2504).

Here, the contrast-enhanced medical image obtained at another point of time is divided into predetermined anatomical entities, that is, lymph node and blood vessel regions (2512), and subjected to the transformation and spread (2503) for matching coordinates of these two medical images, and the region correction (2504). Here, the data subjected to the image registration (2522) and the transformation and spread (2523) from the standard image/model are further utilized. When the obtained region correction (2504) is completed, a fused image is displayed as a registration image (2505).

As the image is sequentially subjected to the registration, the transformation and the spread, and the correction, comparison in change of the lymph node between the contrast-enhanced medical image obtained at another point of time and the non-contrast medical image obtained at this time is quantified (2513), and the data from the standard image/model is further utilized in the quantification, thereby displaying a quantification result (2514).

Figure 26:
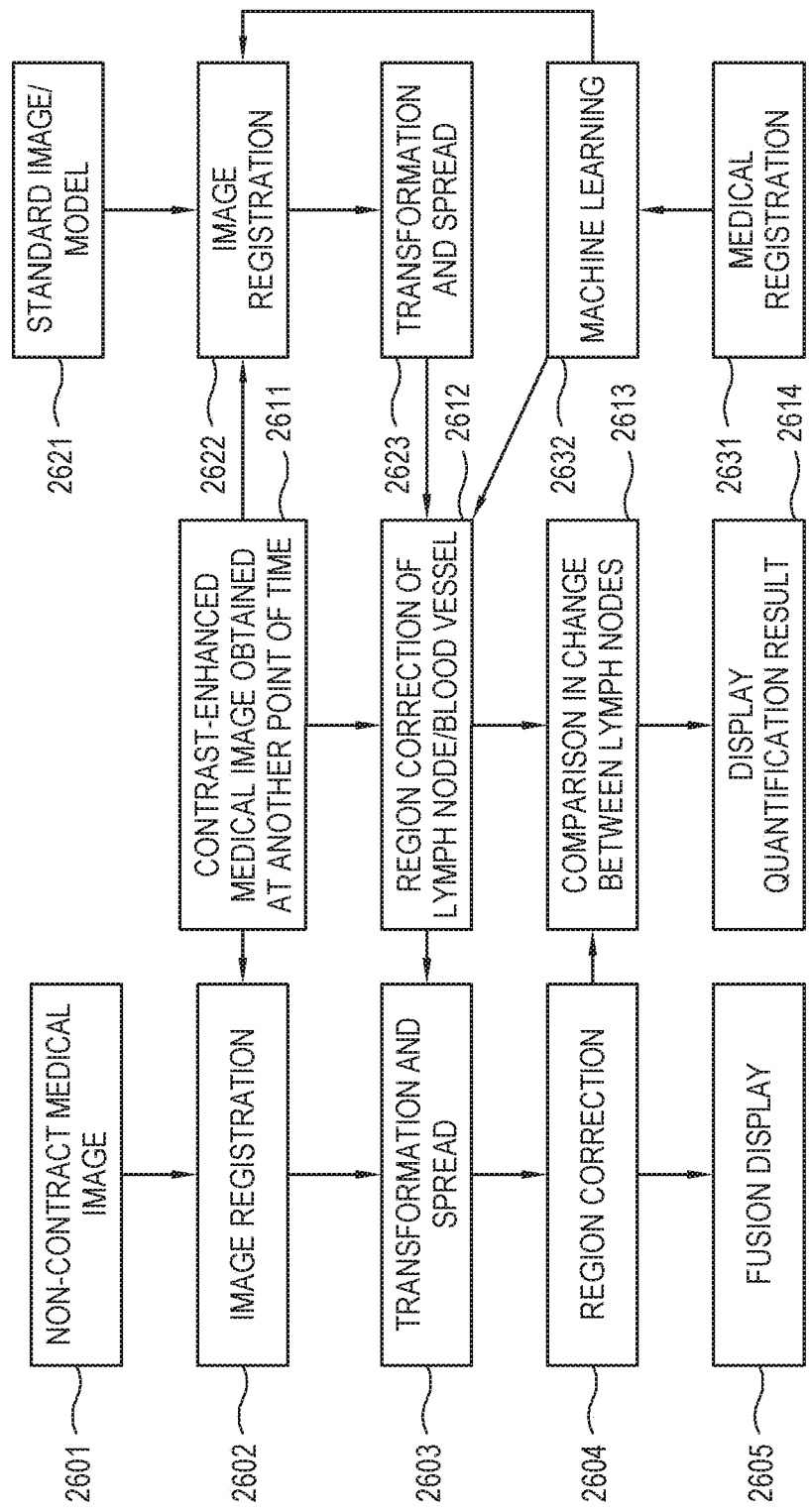

In yet another embodiment shown in FIG. 26, when there are no contrast-enhanced images obtained by photographing an object, two or more non-contrast medical images t1 and t2 are subjected to registration, and the standard image/model 2621 and/or the medical image database (2631) may be utilized for improving accuracy.

That is, according to the embodiment of FIG. 26, severity of lesion in the anatomical entity is determined and distinguishably displayed in image-taking order by applying registration to two or more non-contrast images taken at different points t1 and t2 of time.

Specifically, the controller 1010 of the medical image display device 100 obtains a non-contrast medical image 2601 taken at the point t2 of current time and the non-contrast medical image 2611 taken at the point t1 in the past, and generates a fusion display based on their registration.

A process of generating the fusion display may include image registration (2602) between the non-contrast medical image taken at the point t2 of current time and the non-contrast medical image taken at the point t1 in the past, transformation and spread (2603) of the image generated by the registration, and region correction (2604).

Here, the contrast-enhanced medical image obtained at the time t1 in the past is divided into predetermined anatomical entities, that is, lymph node and blood vessel regions and subjected to the correction (2612), and information stored in the standard image/model 2621 and/or the medical image database (2631) is utilized.

The medical image database 2631 stores various pieces of information, and the controller 1010 assorts data (including images) having conditions (age, sex, severity of lesion, etc. of an object) similar to the object among the pieces of stored information, and performs machine learning for predicting data through a training process using the assorted data (2632).

The controller 1010 loads a plurality of images corresponding to conditions (e.g. age, sex, severity of lesion, etc. of an object) similar to the object from data stored in the standard image/model (2621), and applies the image registration (2622) and the transformation and spread (2623) to the loaded images. Here, the process of the image registration (2622) may further use data predicted by the machine learning.

The controller 1010 uses data transformed and spread from the machine learning (2632) and/or the standard image/model, and corrects the lymph node/the blood vessel region extracted from the non-contrast medical image taken at the point t1 in the past (2612), which may be subjected to the transformation and spread (2602) for matching coordinates of these two medical images and the region correction (2603). When the region correction (2603) is completed, a fused image is displayed as a registration image (2605).

As the image is sequentially subjected to the registration, the transformation and the spread, and the correction, comparison in change of the lymph node between the non-contrast medical image obtained at another point t1 of time and the non-contrast medical image obtained at this point t2 of time is quantified (2613), and the data from the machine learning is further utilized in the quantification, thereby displaying a quantification result (2614)

By the way, the third medical image and/or the fourth medical image generated by the foregoing embodiments of the present disclosure may be stored in the medical image database or the standard image/model, and the stored images may be used in the machine learning or the image registration for distinguishing the anatomical entities in another non-contrast image by registration/transformation/spread of two or more images.

Below, a medical image processing method according to embodiments of the present disclosure will be described with reference to the accompanying drawings.

Figure 27:
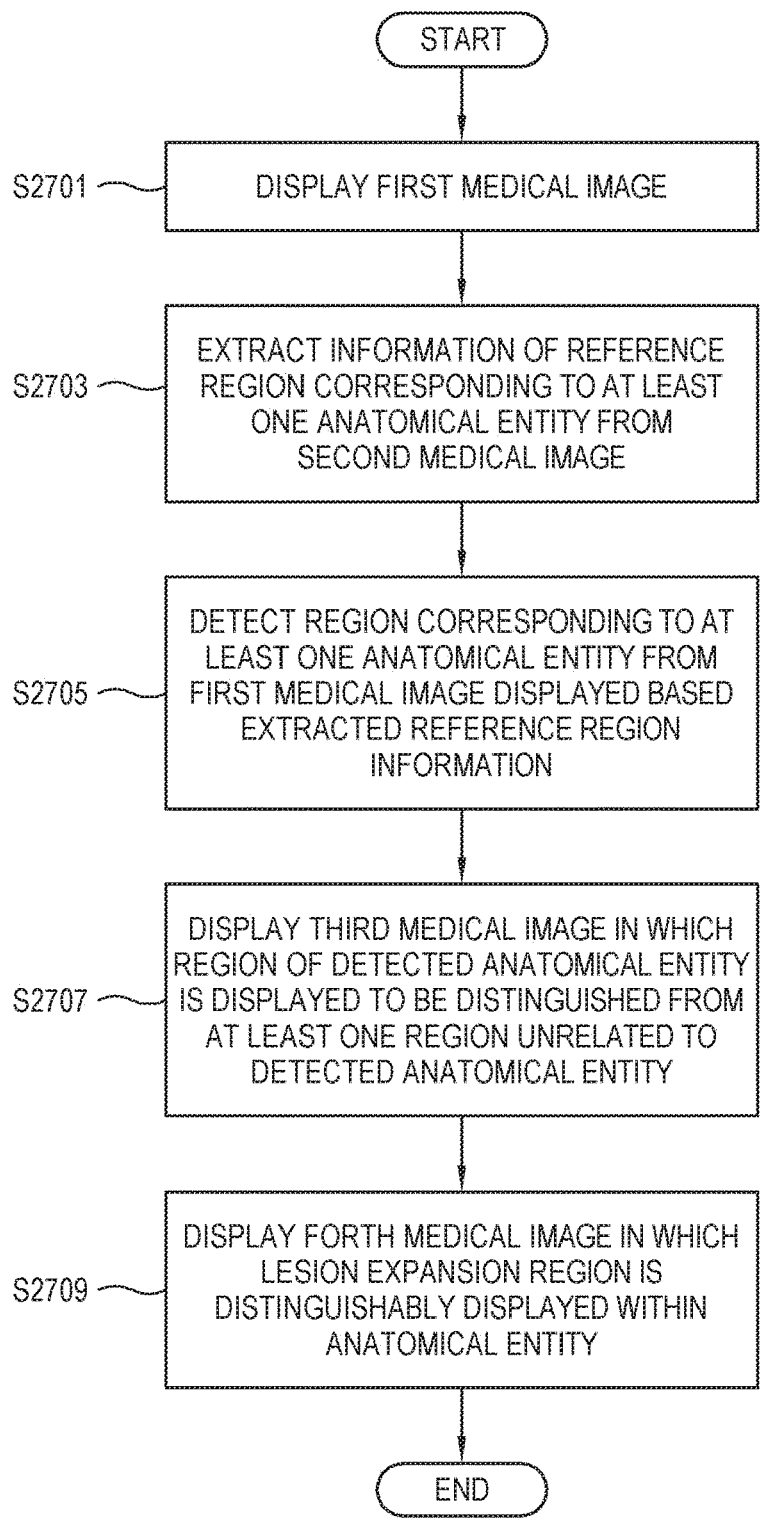
FIG. 27 is a flowchart of a medical image processing method according to one embodiment of the present disclosure.

FIG. 27 is a flowchart of a medical image processing method according to one embodiment of the present disclosure.

As shown in FIG. 27, the display 1020 of the medical image display device 1000 may display a first medical image obtained by photographing an object including at least one anatomical entity (S2701). Here, the first medical image may be a non-contrast medical image.

Under control of the controller 1010, the image processor 1030 extracts reference region information corresponding to at least one anatomical entity from a second medical image used as a reference image for the first medical image displayed in the operation S2701 (S2703). Here, the second medical image may be a contrast-enhanced medical image obtained by photographing an object corresponding to the first medical image at a different point of time. Alternatively, the second medical image may be a standard image generated based on the images having similar conditions to the object. Further, there may be a plurality of anatomical entities from which information is extracted, and the anatomical entities may include a blood vessel, a lymph node, a bronchial tube, etc. In the operation S2703, the reference region information may be extracted corresponding to a predetermined anatomical entity based on brightness levels of pixels in the second medical image.

The controller 1010 controls the image processor 1030 to detect a region corresponding to at least one anatomical entity from the first medical image displayed in the operation S2701 based on the reference region information in the operation S2703 (S2705).

Further, the controller 1010 displays a third medical image where the region detected in the operation S2705 is displayed distinguishably from the regions of the other anatomical entities (S2707). Here, the third medical image, which is generated by registration of the first medical image and the second medical image, may include the display region information about the anatomical entity detected in the operation S2705. Based on the display region information, the controller 1010 controls the display 1020 to display the region of the anatomical entity to be distinguished from at least one region unrelated to the anatomical entity in the third medical image.

The controller 1010 may display a fourth medical image where a lesion expansion region is distinguishably displayed in the anatomical entity distinguishably displayed in the operation S2705 (S2709).

The operations S2707 and S2709 may be performed during the image registration between the first medical image and the second medical image. Further, the third medical image displayed in the operation S2707 corresponds to a result from the homogeneous registration, and the fourth medical image displayed in the operation S2709 corresponds to a result from the in-homogeneous registration.

The medical image registration in the operations S2707 and S2709 may be performed using a predetermined transformation model parameter, and repetitively performed until the similarity measurement function between the first medical image and the second medical image has the maximum result value or until the cost function between the first medical image and the second medical image has the minimum result value. Further, the coordinate systems of the first medical image and the second medical image are subjected to mapping, the homogeneous registration for obtaining the transformation formula information, in which the unique characteristics of the anatomical entity are maintained, and the in-homogeneous registration for obtaining the transformation formula information, in which the pieces of information of the first medical image and the second medical image are exactly matched, are performed in sequence.

According to the foregoing embodiments of the present disclosure, there is provided a function of separately displaying the anatomical entities, for example, the lymph node and the blood vessel region, based on the non-contrast image. Further, there are a follow-up examination and quantification (e.g. volume, density, shape, distribution variation, etc.) functions based on the non-contrast image for the lymph node.

The features according to the embodiments of the present disclosure may be partially or entirely coupled or combined, and technically variously interworked and driven as fully appreciated by those skilled in the art. Further, the exemplary embodiments may be materialized independently of each other or realized to interwork together.

Thus, according to one embodiment of the present disclosure, it is possible to apply the follow-up examination for the lymph node to patients whose kidneys function poorly and who are difficult to actively get the contrast medium.

Further, probability of a misdiagnosis of lymph node-related diseases is low even though it is based on the non-contrast image, thereby improving a diagnosis system (under/over-estimation) and enhancing accuracy of a diagnosis.

Further, the present embodiments are applicable to a non-contrast image for general examination, and utilized in a diagnosis or the like of cancer metastasis and the like cancer diseases.

By the way, the foregoing exemplary embodiments of the present disclosure may be realized by a computer readable recording medium. The computer-readable recording medium includes a storage medium for storing data readable by a transmission medium and a computer system. The transmission medium may be materialized by a wired/wireless network where computer systems are linked.

The foregoing exemplary embodiments may be realized by hardware and combination between hardware and software. As the hardware, the controller 1010 may include a nonvolatile memory in which a computer program is stored as the software, a RAM in which the computer program stored in the nonvolatile memory is loaded, and a CPU for executing the computer program loaded in the RAM. The nonvolatile memory may include a hard disk drive, a flash memory, a ROM, CD-ROMs, magnetic tapes, a floppy disc, an optical storage, a data transfer device using Internet, etc., but is not limited thereto. The nonvolatile memory is a kind of computer-readable recording medium in which a program readable by a computer of the present disclosure is recorded.

The computer program is a code that is read and executed by the CPU, and includes codes for performing the operations of the controller 1010 such as the operations S1801 to S1809 as shown in FIG. 18 and the operations S2301 to S2309 as shown in FIG. 23.

The computer program may be included in an operating system provided in the medical image display device 1000 or software including a application and/or software interfacing with an external device.

Although the present disclosure has been shown and described through exemplary embodiments, the present disclosure is not limited to the exemplary embodiments and may be variously materialized within the appended claims.

The invention claimed is:

1. A medical image display device comprising:
a display configured to display a first medical image obtained by photographing an object comprising at least one anatomical entity; and
at least one processor configured to:
extract reference region information corresponding to the anatomical entity from at least one contrast enhanced second medical image obtained by photographing the object of the first medical image at a previous point of time and used as a reference image for the first medical image,
detect a region corresponding to the anatomical entity from the first medical image based on the extracted reference region information, and
control the display to display the region of the detected anatomical entity to be distinguishable from at least region unrelated to the anatomical entity.

2. The medical image display device of claim 1, wherein the at least one processor is further configured to:
generate a third medical image comprising display region information about the detected anatomical entity in the first medical image by registration between the first medical image and the second medical image, and
control the display to display the region of the detected anatomical entity to be distinguishable from at least one region unrelated to the anatomical entity in the third medical image generated based on the display region information.

3. The medical image display device of claim 1,
wherein the anatomical entity is given in plural, and
wherein the display displays regions of the plurality of anatomical entities to be distinguishable.

4. The medical image display device of claim 1, wherein the first medical image comprises a non-contrast medical image.

5. The medical image display device of claim 1,
wherein the display displays the region of the detected anatomical entity to be distinguishable with at least one of a color, a pattern, a pointer, a highlight or an animation effect from the at least one region unrelated to the anatomical entity, and
wherein the distinguishable display for the region of the anatomical entity is activated or inactivated by a user's selection.

6. The medical image display device of claim 1, wherein the at least one processor is further configured to:
detect a lesion expansion region from the region of the anatomical entity, and
control the display to display the detected lesion expansion region to be distinguishable within the region of the anatomical entity.

7. The medical image display device of claim 2, wherein the at least one processor is further configured to employ a predetermined transformation model parameter for performing image registration to maximize a result value of a similarity measurement function between the first medical image and the second medical image.

8. The medical image display device of claim 2, wherein the at least one processor is further configured to employ a predetermined transformation model parameter for performing image registration to minimize a result value of a cost function between the first medical image and the second medical image.

9. The medical image display device of claim 2, wherein the at least one processor is further configured to:

make coordinate systems of the first medical image and the second medical image be subjected to mapping, and perform homogeneous registration, in which image characteristics of the second medical image are maintained and matched with the first medical image, with regard to the first medical image and the second medical image of which the coordinate systems are subjected to the mapping.

10. The medical image display device of claim 9, wherein the at least one processor is further configured to perform in-homogeneous registration, in which image characteristics of the second medical image are transformed and exactly matched with the first medical image, with regard to the first medical image and the second medical image which are subjected to the homogeneous registration.

11. A medical image processing method comprising:
displaying a first medical image obtained by photographing an object comprising at least one anatomical entity;
extracting reference region information corresponding to the anatomical entity from at least one second contrast enhanced medical image obtained by photographing the object of the first medical image at a previous point of time and used as a reference image for the first medical image;
detecting a region corresponding to the anatomical entity from the first medical image based on the extracted reference region information; and
displaying the region of the detected anatomical entity to be distinguishable from at least one region unrelated to the anatomical entity.

12. The medical image processing method of claim 11, further comprising generating a third medical image comprising display region information about the detected anatomical entity in the first medical image by registration between the first medical image and the second medical image, wherein the distinguishable displaying comprises displaying the region of the detected anatomical entity to be distinguishable from at least one region unrelated to the anatomical entity in the third medical image generated based on the display region information.

13. The medical image processing method of claim 11, wherein the first medical image comprises a non-contrast medical image.

14. The medical image processing method of claim 11, further comprising:
detecting a lesion expansion region from the region of the anatomical entity; and
displaying the detected lesion expansion region to be distinguishable within the region of the anatomical entity.

15. The medical image processing method of claim 12, wherein the generating of the third medical image comprises:
making coordinate systems of the first medical image and the second medical image be subjected to mapping,
performing homogeneous registration, in which image characteristics of the second medical image are maintained and matched with the first medical image, with regard to the first medical image and the second medical image of which the coordinate systems are subjected to the mapping, and
performing in-homogeneous registration, in which image characteristics of the second medical image are transformed and exactly matched with the first medical image, with regard to the first medical image and the second medical image which are subjected to the homogeneous registration.

* * * * *